United States Patent
Vaisman et al.

(10) Patent No.: US 9,651,504 B2
(45) Date of Patent: May 16, 2017

(54) FANO RESONANCE MICROWAVE SPECTROSCOPY OF HIGH ABSORPTION MATTER

(71) Applicant: B.G. NEGEV TECHNOLOGIES AND APPLICATIONS LTD., AT BEN-GURION UNIVERSITY, Beer Sheva (IL)

(72) Inventors: Guy Vaisman, Ashdod (IL); Evgeny Elman, Kfar-Saba (IL); Elad Hollander, Hod-Hasharon (IL); Eugene O. Kamenetskii, Beer Sheva (IL); Reuven Shavit, Pardesia (IL)

(73) Assignee: B.G. Negev Technologies and Applications Ltd., at Ben-Gurion University, Beer Sheva (IL)

( * ) Notice: Subject to any disclaimer, the term of this patent is extended or adjusted under 35 U.S.C. 154(b) by 28 days.

(21) Appl. No.: 14/811,910

(22) Filed: Jul. 29, 2015

(65) Prior Publication Data

US 2016/0033422 A1  Feb. 4, 2016

Related U.S. Application Data

(60) Provisional application No. 62/030,630, filed on Jul. 30, 2014.

(51) Int. Cl.
*G01R 27/26* (2006.01)
*G01N 22/00* (2006.01)

(52) U.S. Cl.
CPC .................. *G01N 22/00* (2013.01)

(58) Field of Classification Search
CPC .... G06F 1/16; G06F 3/01; G09G 1/00; H05K 13/046; H05K 7/02; H04B 1/3833; G01N 22/00; G01D 5/242; H04L 67/12
See application file for complete search history.

(56) References Cited

U.S. PATENT DOCUMENTS 3,475,642 A * 10/1969 Karp ................. H01J 23/24
  315/3.5
4,559,490 A * 12/1985 Gannon ............. H01P 1/2084
  333/202

OTHER PUBLICATIONS

U. Fano, Effects of Configuration Interaction on Intensities and Phase Shifts, Phys. Rev. 124, pp. 1866-1878 (1961).
C. Wu, A. B. Khanikaev, R. Adato, N. Arju, A. A. Yanik, H. Altug, and G. Shvets, Fano-resonant asymmetric metamaterials for ultrasensitive spectroscopy and identification of molecular monolayers, Nature Mater. vol. 11, pp. 69-75 (2012).
A. E. Cetin and H. Altug, Fano Resonant Ring/Disk Plasmonic Nanocavities on Conducting Substrates for Advanced Biosensing, ASC Nano vol. 6, pp. 9989-9995 (2012).

(Continued)

*Primary Examiner* — Vinh Nguyen
(74) *Attorney, Agent, or Firm* — Roach Brown McCarthy & Gruber, P.C.; Kevin D. McCarthy

(57) ABSTRACT

The invention is a method of Fano resonance microwave spectroscopy of high absorption matter. The method comprises: embedding a magnetic-dipolar-mode (MDM) ferrite disk in the microwave cavity, loading a sample of the high absorption matter in the microwave cavity, using a bias magnetic field to tune the MDM resonance frequency of the ferrite disk to the resonance frequency of the cavity; and observing the symmetric Lorentz-like lineshape of the resonance peaks that are obtained.

14 Claims, 19 Drawing Sheets

(56) References Cited

OTHER PUBLICATIONS

S. Ray and J. Behari, Microwave absorption in lossy liquids, Phys. Med. Biol. vol. 31, pp. 1031-1040 (1986).

L. L. van Zandt, Resonant Microwave Absorption by Dissolved DNA, Phys. Rev. Lett. vol. 57, pp. 2085-2087 (1986).

C.-T. Zhang, Harmonic and subharmonic resonances of microwave absorption in DNA, Phys. Rev. A vol. 40, pp. 2148-2153 (1989).

C. Gabriel, E.H. Grant, R. Tata, P.R. Brown, B. Gestblom, and E. Noreland, Dielectric behavior of aqueous solutions of plasmid DNA at microwave frequencies, Biophys. J. vol. 55, pp. 29-34 (1989).

R. K. Adair, Vibrational Resonances in Biological Systems at Microwave Frequencies, Biophys. J. vol. 82, pp. 1147-1152 (2002).

J. Kim, A. Babajanyan, A. Hovsepyan, K. Lee, and B. Friedman, Microwave dielectric resonator biosensor for aqueous glucose solution, Rev. Sci. Instr. 79, pp. 086107 1-3 (2008).

C. Dalmay, M. Cheray, A. Pothier, F. Lalloué, M. O. Jauberteau, P. Blondy, Ultra sensitive biosensor based on impedance spectroscopy at microwave frequencies for cell scale analysis, Sens. and Actuat. A: Phys. 162, pp. 189-197 (2010).

H.-J. Lee, H.-S. Lee, K.-H. Yoo, and J.-G. Yook, DNA sensing using split-ring resonator alone at microwave regime, J. Appl. Phys. 108, pp. 014908 1-6 (2010).

H.-J. Lee, J.-H. Lee, and H.-I. Jung, A symmetric metamaterial element-based RF biosensor for rapid and label-free detection, Appl. Phys. Lett. 99, pp. 163703 1-3 (2011).

S. Kim, J. Kim, K. Kim, J.-H. Lee, A. Babajanyan, B. Friedman, K. Lee, In vitro monitoring of goat-blood glycemia with a microwave Biosensor, Curr. Appl. Phys. 14, pp. 563-569 (2014).

B. Yu. Kapilevich, S. G. Ogourtsov, V. G. Belenky, A. B. Maslenikov, and A. S. Omar, Accurate Microwave Resonant Method for Complex Permittivity Measurements of Liquids, IEEE Trans. Microw. Theor. Techn. vol. 48 No. 11, pp. 2159-2164 (Nov. 2000).

E. Ermilova, F. F. Bier and R. Hölzel, Dielectric measurements of aqueous DNA solutions up to 110 GHz, Phys. Chem. Chem. Phys. 16, pp. 11256-11264 (2014).

L. D. Landau and E. M. Lifshitz, Electrodynamics of Continuous Media, 2nd ed., pp. 253-256 (Pergamon Press, Oxford, 1984).

E. O. Kamenetskii, Energy eigenstates of magnetostatic waves and oscillations, Phys. Rev. E vol. 63, pp. 066612 1-10 (2001).

E. O. Kamenetskii, M. Sigalov, and R. Shavit, Quantum confinement of magnetic-dipolar oscillations in ferrite discs, J. Phys.: Condens. Matter 17, pp. 2211-2231 (2005).

E. O. Kamenetskii, Vortices and chirality of magnetostatic modes in quasi-2D ferrite disc particles, J. Phys. A: Math. and Theor. 40, pp. 6539-6559, (2007).

E. O. Kamenetskii, M. Sigalov, and R. Shavit, Manipulating microwaves with magnetic-dipolar-mode vortices, Phys. Rev. A 81, pp. 053823 1-15 (2010).

E. O. Kamenetskii, Helical-mode magnetostatic resonances in small ferrite particles and singular metamaterials, J. Phys.: Condens. Matter 22, pp. 486005 1-18 (2010).

E. O. Kamenetskii, R. Joffe, and R. Shavit, Coupled states of electromagnetic fields with magnetic-dipolar-mode vortices: Magnetic-dipolar-mode vortex polaritons, Phys. Rev. A 84, pp. 023836 1-18 (2011).

E. O. Kamenetskii, E. O., R. Joffe, and R. Shavit, Microwave magnetoelectric fields and their role in the matter-field interaction, Phys. Rev. E 87, pp. 023201 1-31 (2013).

E. O. Kamenetskii, A. K. Saha, and I. Awai, Interaction of magnetic-dipolar modes with microwave-cavity electromagnetic fields, Phys. Lett. A 332, pp. 303-309 (2004).

M. Sigalov, E. O. Kamenetskii, and R. Shavit, Eigen electric moments and magnetic-dipolar vortices in quasi-2D ferrite disks, Appl. Phys. B 93, pp. 339-343 (2008).

M. Berezin, E. O. Kamenetskii, and R. Shavit, Topological properties of microwave magnetoelectric fields, Phys. Rev. E 89, pp. 023207 1-16 (2014).

E. O. Kamenetskii, G. Vaisman, and R. Shavit, Fano resonances of microwave structures with embedded magneto-dipolar quantum dots, J. Appl. Phys. 114, pp. 173902 1-12 (2013).

M. Sigalov, E. O. Kamenetskii, and R. Shavit, Magnetic-dipolar and electromagnetic vortices in quasi-2D ferrite discs, J. Phys.: Condens. Matter 21, pp. 016003 1-15 (2009).

E. O. Kamenetskii, M. Sigalov, and R. Shavit, Tellegen particles and magnetoelectric metamaterials, J. Appl. Phys. 105, pp. 013537 1-15 (2009).

J. F. Dillon, Magnetostatic Modes in Disks and Rods, J. of Appl. Phys. vol. 31, No. 9, pp. 1605-1614 (Sep. 1960).

T. Yukawa and K. Abe, FMR spectrum of magnetostatic waves in a normally magnetized YIG disk, J. Appl. Phys. vol. 45, No. 7, pp. 3146-3153 (Jul. 1974).

S. E. Harris, Electromagnetically Induced Transparency, Phys. Today 50 (7), pp. 36-42 (Jul. 1997).

R. Hutcheon, M. de Jong, and F. Adams, A system for rapid measurments of RF and microwave properties up to 14000C, J. of Microw. Power and Electromagn. Energy, vol. 27, No. 2, pp. 87-92 (1992).

G. Vaisman, E. O. Kamenetskii, and R. Shavit, Magnetic-dipolar-mode Fano resonances for microwave spectroscopy of high absorption matter, J. Phys. D: Appl. Phys. 48, pp. 115003 1-13 (2015).

H. Torun, F. C. Top, G. Dundar, and A. D. Yalcinkaya, An antenna-coupled split-ring resonator for biosensing, J. Appl. Phys. 116, pp. 124701 1-6 (2014).

\* cited by examiner

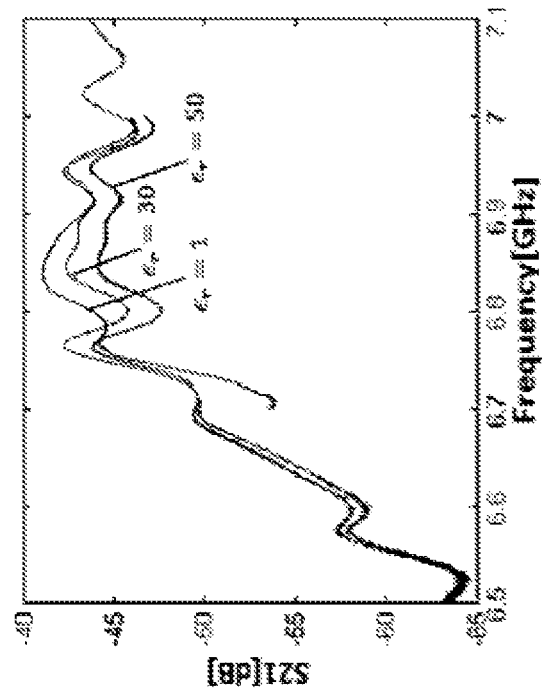
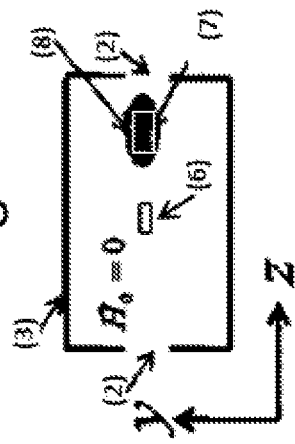
Fig. 3a
Fig. 3c
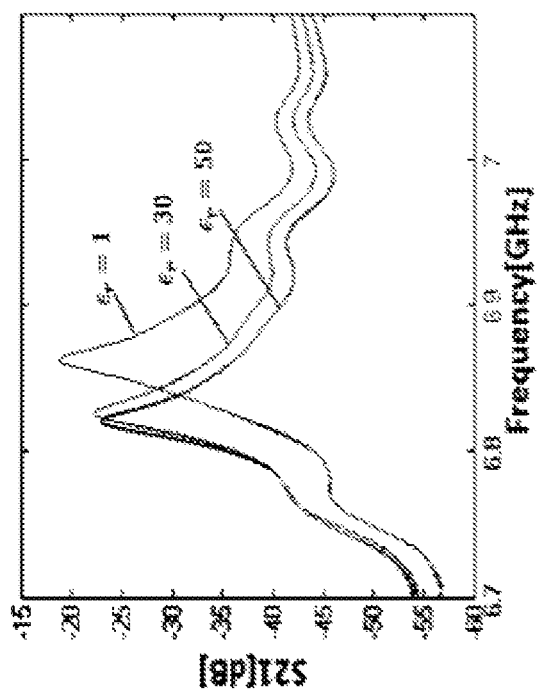
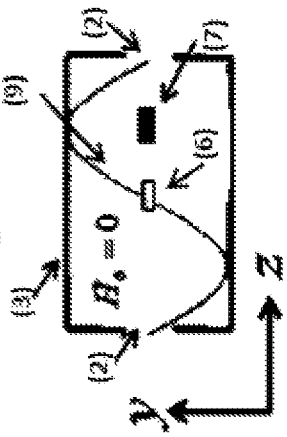
Fig. 3b
Fig. 3d

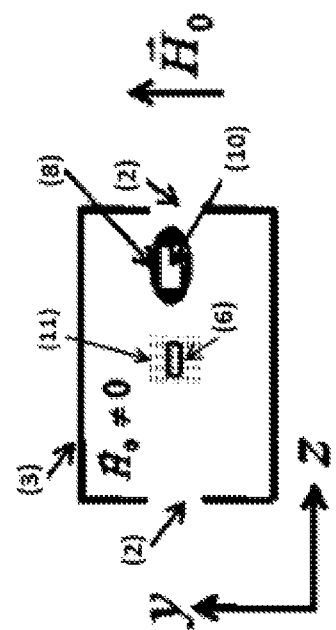
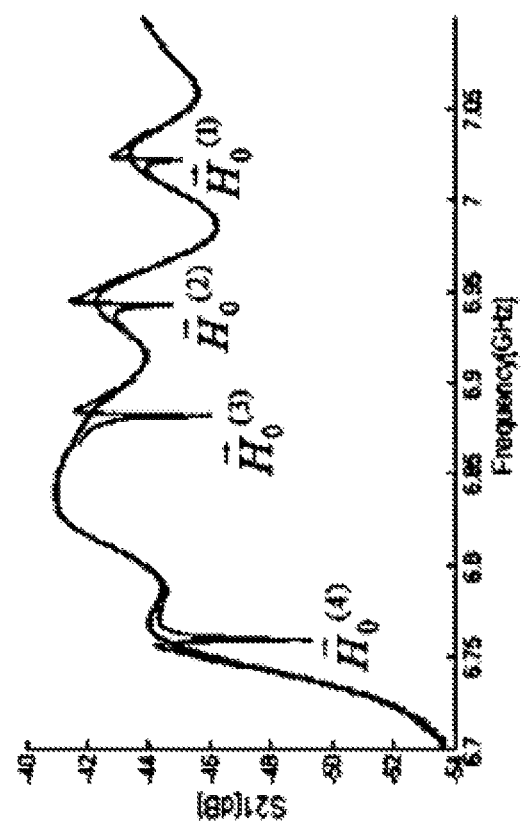
Fig. 4a
Fig. 4b

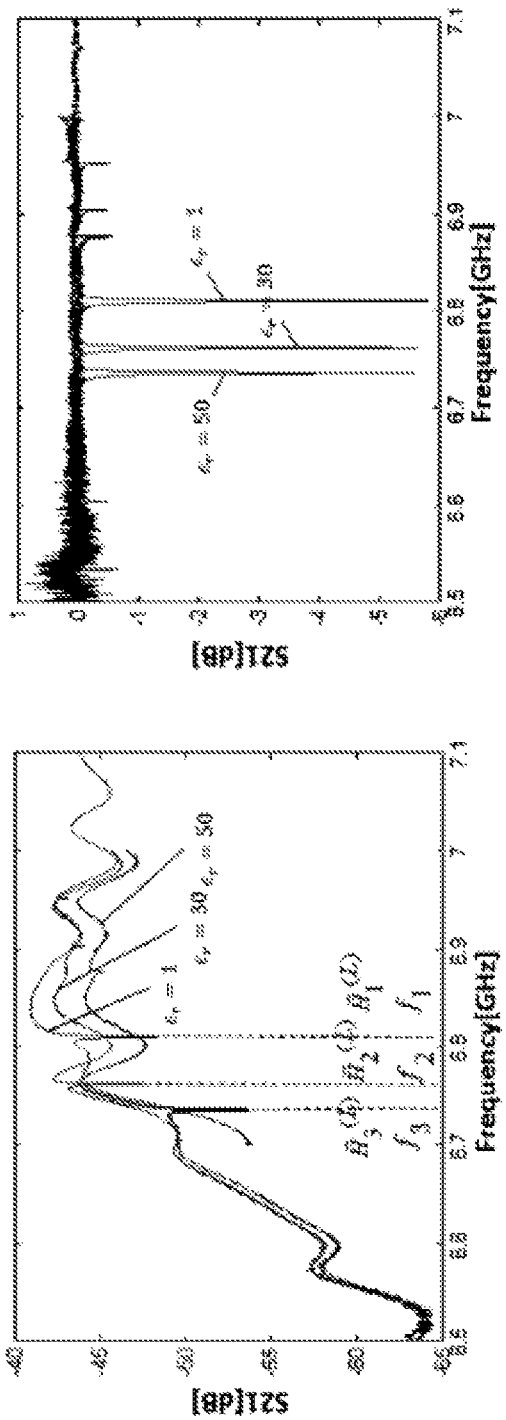
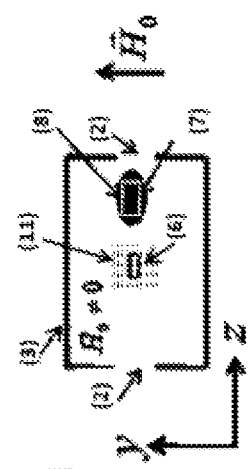
Fig. 5a   Fig. 5b   Fig. 5c

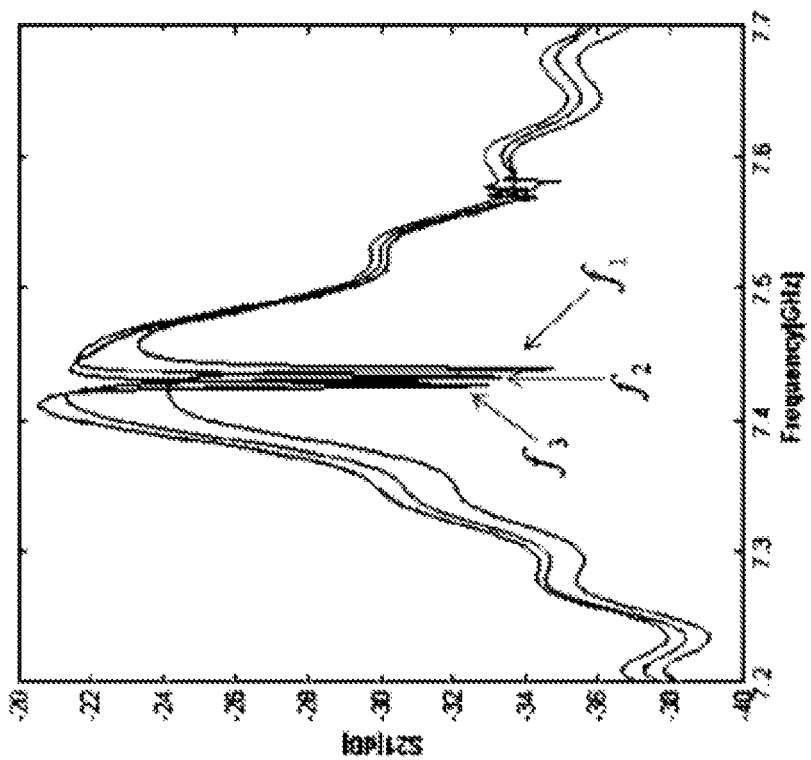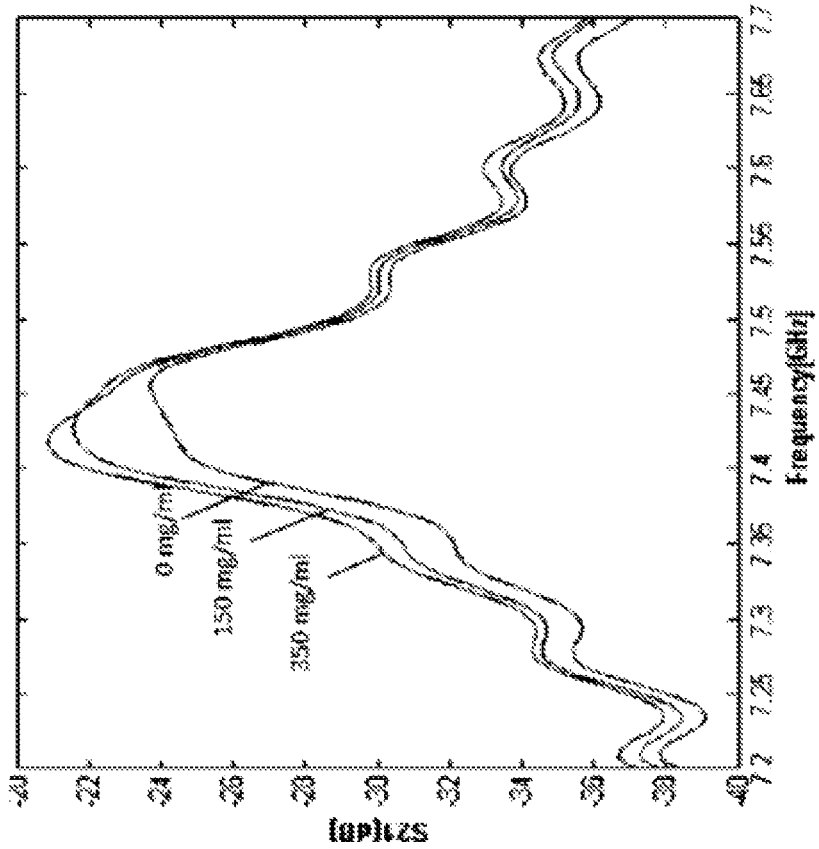
Fig. 7b
Fig. 7a

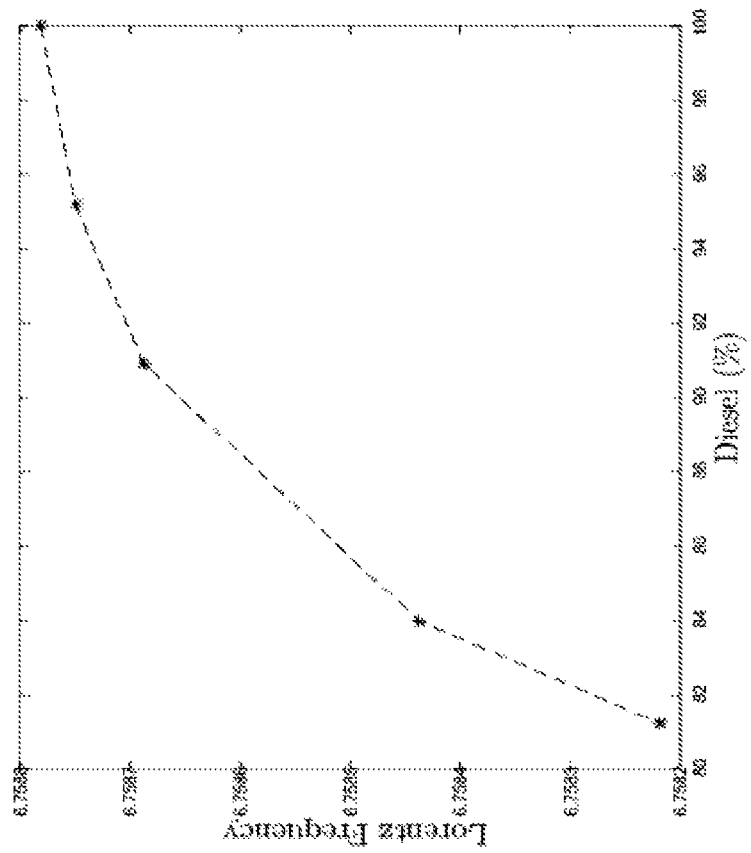
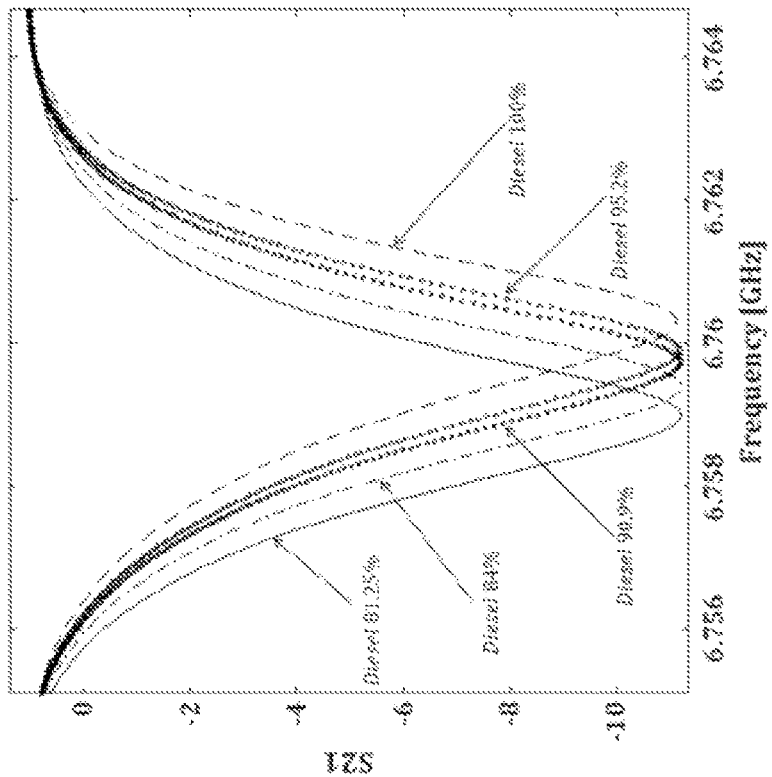
Fig. 13b
Fig. 13a

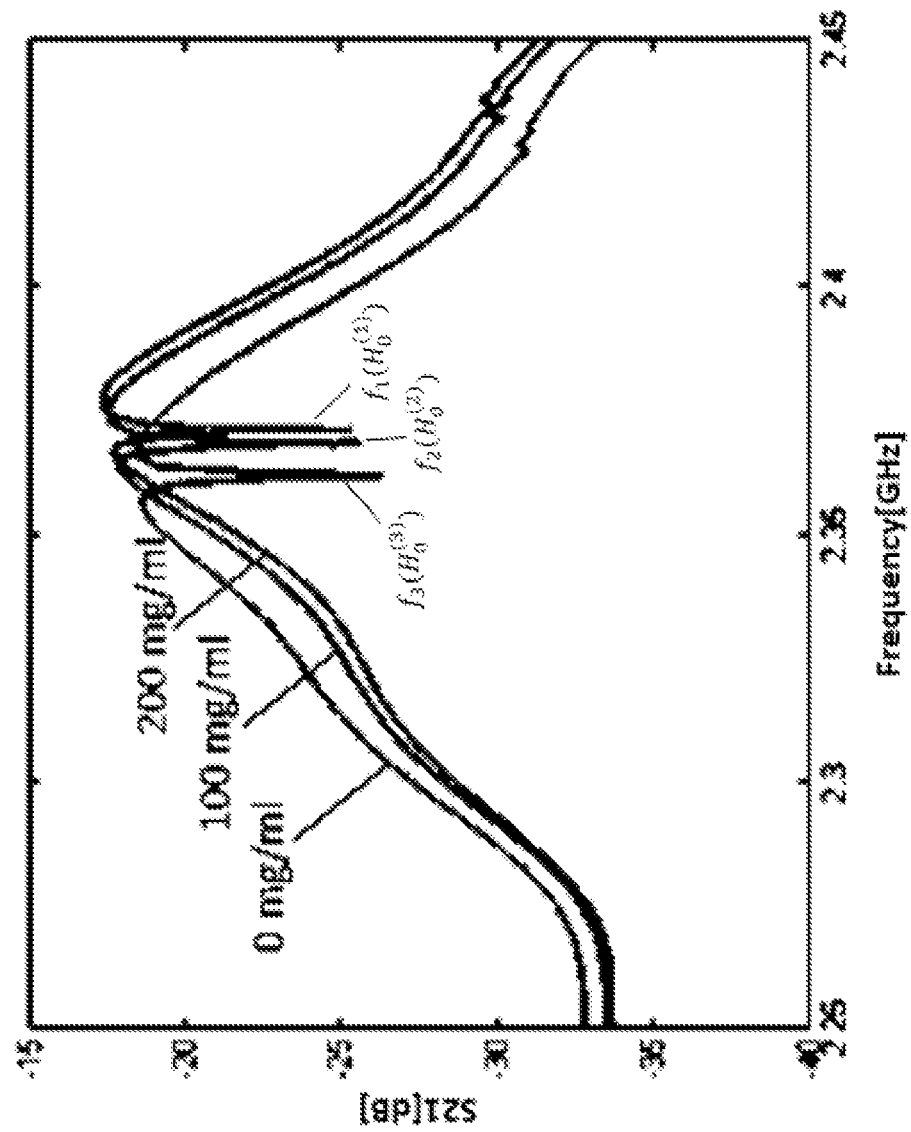

FANO RESONANCE MICROWAVE SPECTROSCOPY OF HIGH ABSORPTION MATTER

FIELD OF THE INVENTION

The invention is from the field of microwave spectroscopy. Specifically the invention relates to microwave spectroscopy characterization of lossy materials including biological liquids.

BACKGROUND OF THE INVENTION

Publications and other reference materials referred to herein are numerically referenced in the following text and respectively grouped in the appended Bibliography which immediately precedes the claims.

Fano resonances arise when two transmission pathways, a broad band continuum and a narrow band resonance, interfere with each other [1]. When one of the channels is a highly damped resonance process, its exact resonant frequency is difficult to detect and such a channel can be considered as a broad band continuum. The physical origin of Fano resonances can be understood simply from the dynamics of a system of coupled oscillators. The Fano-resonant phenomenon appears as a notch in the absorption spectrum when the incident electromagnetic wave couples to a strongly damped oscillator, which in turn is coupled to a weakly damped mode. The resulting effective coupling between the two modes is dispersive, i.e., it depends strongly on the frequency in a narrow interval around the frequency of the weakly damped oscillator and gives rise to a strong modulation of the absorption spectrum. Presently, these effects are widely used in optical spectroscopy of biological structures [2, 3]. At the same time, there are no publications, to the best of the inventor's knowledge, on the Fano-resonant spectroscopy of biological structures in microwaves.

Study of microwave properties of biological liquids is one of the most important problems in biophysics. Microwave absorption is primarily a tool for observing and measuring different kinetic processes in biological liquids. It may concern molecule rotational transitions and vibrational resonances in biological systems. Microwave absorption resonances are observed in aqueous solutions of DNA [4-7]. The success of a spectroscopic technique depends on two main problems: one is the availability of accurate data over the required frequency range while the other is the ability to unambiguously interpret this data. These two problems have a special aspect in spectroscopic characterization of high lossy materials. The temporal and spatial resonant nature of an electromagnetic standing wave within a dissipative media is obscure and incoherent. Spatially, regions with maximum magnetic (electric) field and null electric (magnetic) field can no longer be well defined and separated. One of the topical subjects on the lossy-material characterization concerns microwave analyses of biological liquids. Proper correlation of the measured parameters with structural characteristics of chemical and biological objects in microwaves appears as a serious problem. Nowadays, microwave biosensing is mainly represented by the microwave-cavity technique and the transmission/reflection technique [8-15]. The microwave-cavity technique is based on the well-known perturbation method used for measuring dielectric properties of materials. The resonant techniques, however, are not suitable for high-lossy liquids because the resonance peak is so broad that the perturbation characteristics cannot be measured correctly. Also, interpretation of the data obtained from the transmission/reflection technique cannot be considered as sufficiently suitable for high-lossy liquids.

In numerous microwave experiments, a problem of the high-lossy-material characterization is formulated in order to obtain data on the permittivity and permeability parameters, which are represented as a combination of real and imaginary parts, i.e. $\in'$, $\in''$ and $\mu'$, $\mu''$. It appears, however, that such representation of parameters and, moreover, interpretation that these data properly characterize high-lossy materials may be beyond a physical meaning. This statement is clarified by the following consideration. It is known that electromagnetic processes in a non-conductive medium are described, energetically, by Poyning's theorem which, when represented in the form of the continuous equation:

$$\vec{\nabla} \cdot \vec{S} = \frac{\partial w}{\partial t} + q, \qquad (1)$$

shows that divergence of the power flow density $\vec{S}$ is determined by two quantities: time variation of the electromagnetic-field density w and density the dissipation losses q. For an isotropic temporally dispersive medium, described by constitutive parameters $\in(\omega)=\in'(\omega)+i\in''(\omega)$ and $\mu(\omega)=\mu'(\omega)+i\mu'(\omega)$, the two terms in the right-hand side of Eq. (1) have definite physical meaning (and so can be considered separately) only when $$|\in''(\omega)| \ll |\in'(\omega)| \text{ and } |\mu''(\omega)| \ll |\mu'(\omega)| \qquad (2)$$

The frequency regions where $|\in''(\omega)|$ and $|\mu''(\omega)|$ are small compared to $|\in'(\omega)|$ are $|\mu'(\omega)|$ are called the regions of transparency of a medium. Only inside transparency regions can one separately introduce a notion of the electromagnetic-field density w (which is related to the real-part quantities $\in'$ and $\in'$) and a notion of density the dissipation losses q (which is related to the imaginary-part quantities $\in''$ and $\mu''$). The energy balance equation (1) for such a transparent medium is described by quasi-monochromatic fields [16]. For a non-transparent medium (or in a frequency region of medium non-transparency), relations (2) are unrealizable and one cannot describe the right-hand side of Eq. (1) by two separate and physically justified terms. This is the case of a high lossy (or high absorption) medium. In a high lossy medium, one cannot state that the electromagnetic-field density w and density the dissipation losses q are separate notions with definite physical meaning. In such a case, there is no meaning to consider quantities $\in'$ and $\mu'$ as physical parameters related to energy accumulation and quantities $\in''$ and $\mu''$ as physical parameters related to energy dissipation.

In all the known experiments for characterization of high-lossy material parameters, the quasi-monochromatic fields are not used. A decay and a frequency shift, observed in these microwave experiments, are the quantities which describe the high-lossy materials very indirectly. Two basic strategic questions are thus posed: (a) What is the physical meaning of the constitutive parameters characterizing electromagnetic processes in high lossy materials? (b) How can these parameters be precisely measured?

The use of a small ferrite-disk scatterer with internal magneto-dipolar-mode (MDM) resonances in the channel of microwave propagation changes the transmission dramatically. Recently, it was shown that mesoscopic quasi-2D ferrite disks, distinguishing by multi-resonance MDM oscillations, demonstrate unique properties of artificial atomic structures: energy eigenstates, eigen power-flow vortices and eigen helicity parameters [17-23]. These oscillations can be observed as the frequency-domain spectrum at a constant bias magnetic field or as the magnetic-field-domain spectrum at a constant frequency. For electromagnetic waves irradiating a quasi-2D MDM disk, this small ferrite sample appears as a topological defect with time symmetry breaking. Long radiative lifetimes of MDMs combine strong subwavelength confinement of electromagnetic energy with a narrow spectral line width and may carry the signature of Fano resonances [22-26]. Interaction of the MDM ferrite particle with its environment has a deep analogy with the Fano-resonance interference observed in natural and artificial atomic structures [27].

MDM oscillations in a quasi-2D ferrite disk are macroscopically quantized states. Long range dipole-dipole correlation in position of electron spins in a ferromagnetic sample can be treated in terms of collective excitations of the system as a whole. If the sample is sufficiently small so that the dephasing length $L_{ph}$ of the magnetic dipole-dipole interaction exceeds the sample size, this interaction is non-local on the scale of $L_{ph}$. This is a feature of mesoscopic ferrite samples, i.e., samples with linear dimensions smaller then $L_{ph}$ but still much larger than the exchange-interaction scales. MDMs in a quasi-2D ferrite disk possess unique physical properties. Being the energy-eigenstate oscillations, they also are characterized by topologically distinct structures of the fields. There are the rotating field configurations with power-flow vortices. At the MDM resonances, one observes power-flow whirlpools in the vicinity of a ferrite disk. For an incident EM wave, such a vortex topological singularity acts as a trap, providing strong subwavelength confinement and symmetry breakings of the microwave field [17-23, 28, 29].

For a MDM ferrite particle placed inside a microwave cavity with sufficiently low quality factor Q, one can observe the Fano-interference effects in microwave scattering. The spectrum of the MDM oscillations in a ferrite-disk particle is very rich [30, 31]. It contains different types of modes: the radial, azimuthal, and thickness modes [18]. Herein only the case of interaction of the cavity oscillation with the main mode in the MDM-spectrum sequence is considered.

In a widely used microwave cavity technique to determine the complex permittivity material parameters, the perturbation approach is commonly applied, which is characterized with limitation on permittivity and losses values as well as sample dimensions. The perturbation theory requires that sample permittivity, losses values and dimensions should be small enough so that the field distribution inside the empty cavity changes slightly when the cavity is loaded. Only with this limitation, the perturbation technique permits linkage via a simple formula between changes in the resonant frequency and loaded factor determined by the sample.

An example of such a formula, is [33]:

$$\frac{\Delta f}{f_0} + \frac{1}{2}i\Delta\frac{1}{Q} = k\frac{-\chi_e}{(1+F_{sh}\chi_e)} \quad (3)$$

where $\chi_e = \chi_e' - i\chi_e''$ is the complex dielectric susceptibility, $f_0$ is the frequency of an unloaded cavity, $\Delta f$ and $$\Delta\frac{1}{Q}$$

are, respectively, the frequency and quality-factor shifts due to dielectric loading, $F_{sh}$ is the constant dependent on the sample shape, and k is a calibration constant. It can be seen that both the frequency shift and the quality-factor shift depend on both the real and imaginary parts of the dielectric susceptibility. Separate experimental evaluation of these two kinds of shifts is possible only for small material losses. For high-lossy materials, the cavity resonance curve becomes so wide that evaluation of the quality-factor shift cannot presume exact evaluation of the frequency shift. Moreover, since the cavity resonance curve is wide, other resonances (originated, for example, from the terminal connectors) become prominent and an accurate detection of the resonant frequency shift appears to be very difficult.

This and the fact that in known standard microwave experiments, high-lossy material characteristics not only cannot be measured accurately, but also cannot be interpreted physically corrected (assuming that there are the real and imaginary parts of the permittivity and permeability parameters), there arises a need for realization of novel and appropriate microwave techniques for measuring properties of high-lossy materials. Initial studies of such a novel technique are shown in Ref. [34].

It is a purpose of the present invention to provide a method for microwave spectroscopy characterization of lossy materials including biological liquids.

Further purposes and advantages of this invention will appear as the description proceeds.

SUMMARY OF THE INVENTION

In a first aspect the invention is a method of Fano resonance microwave spectroscopy of high absorption matter. The method comprises the steps of:
a. providing a waveguide microwave cavity with low-quality factor;
b. embedding a magnetic-dipolar-mode (MDM) ferrite disk in the microwave cavity;
c. loading a sample of the high absorption matter in the microwave cavity;
d. providing a bias magnetic field to tune the MDM resonance frequency of the ferrite disk to the resonance frequency of the cavity; and
e. observing the symmetric Lorentz-like lineshape of the resonance peaks that are obtained.

In embodiments of the method of the invention the waveguide microwave cavity is a rectangular waveguide microwave cavity operated in the $TE_{102}$ resonant mode.

In embodiments of the method of the invention the magnetic-dipolar-mode (MDM) ferrite disk is comprised of yttrium-iron-garnet (YIG).

In embodiments of the method of the invention the magnetic-dipolar-mode (MDM) ferrite disk is biased by a normal dc magnetic field.

In embodiments of the method of the invention the magnetic-dipolar-mode (MDM) ferrite disk is located at a maximum of the RF magnetic field of the rectangular waveguide microwave cavity.

In embodiments of the method of the invention the sample of the high absorption matter is located at a maximum of the RF electric field of the rectangular waveguide microwave cavity.

In embodiments of the method of the invention the sample of the high absorption matter is a liquid. In some of these embodiments the liquid is enclosed in a small capsule. In some of these embodiments the liquid continuously flows through the rectangular waveguide microwave cavity via a small diameter tube.

In a second aspect the invention is an apparatus for carrying out the method of the first aspect of the invention. The apparatus comprises:
a. a rectangular waveguide;
b. two irises;
c. a rectangular waveguide microwave cavity defined by the space between the two irises;
d. a RF input port;
e. a RF output port;
f. a yttrium-iron-garnet (YIG) disk locate at a maximum of the RF magnetic field of the rectangular waveguide cavity; and
g. a dielectric sample located at a maximum of the RF electric field of the rectangular waveguide cavity.

In embodiments of the apparatus of the second aspect of the invention the dielectric sample is a liquid enclosed in a small capsule.

In embodiments of the apparatus of the second aspect of the invention the dielectric sample is a liquid that continuously flows through the rectangular waveguide microwave cavity via a small diameter tube. These embodiments additionally comprise a pump, a reservoir and a main line that are connected together to continuously circulate the liquid through the small diameter tube.

In a third aspect the invention is a microstrip structure for carrying out the method of the first aspect of the invention. The microstrip structure comprises:
a. a dielectric substrate;
b. conducting strips on the dielectric substrate;
c. a split ring resonator (SRR) coupled with the conducting strips;
d. a RF input port;
e. a RF output port;
f. an yttrium-iron-garnet (YIG) disk embedded inside the SRR; and
g. a small capsule filled with liquid loaded into the SRR.

All the above and other characteristics and advantages of the invention will be further understood through the following illustrative and non-limitative description of embodiments thereof, with reference to the appended drawings.

BRIEF DESCRIPTION OF THE DRAWINGS

FIG. 3a shows the frequency characteristics of a transmission coefficient when the cavity is loaded with a small low-loss dielectric sample;

FIG. 3b shows the frequency characteristics of a transmission coefficient when the same dielectric samples as shown in FIG. 3a are wrapped by a high-absorption material;

FIG. 3c and FIG. 3d schematically show the experimental setup used to obtain FIG. 3a and FIG. 3b respectively;

FIG. 4a shows the peak positions of the main MDM for different values of the bias magnetic field;

FIG. 4b schematically shows the experimental setup used to obtain the results shown in FIG. 4a;

FIG. 5a shows spectroscopic curves for three different high-lossy material samples;

FIG. 5b shows the normalized spectroscopic curves of FIG. 5a;

FIG. 5c schematically shows the experimental setup used to obtain the results shown in FIG. 5a and FIG. 5b;

FIG. 7a to FIG. 7d correspond to FIG. 6a to FIG. 6d with the exception that in these figures the small capsule contains solutions of different concentrations of glucose in distilled water;

FIG. 11a shows the Lorentz frequencies for different concentrations of NaCl in water;

FIG. 11b is a graph of Lorentz frequencies vs. concentration derived from the results shown in FIG. 11a;

FIG. 12b is a graph of Lorentz frequencies vs. concentration derived from the results shown in FIG. 12a;

FIG. 13a shows the Lorentz frequencies for different concentrations of Diesel fuel concentration in solution with oil;

FIG. 13b is a graph of Lorentz frequencies vs. concentration derived from the results shown in FIG. 13a;

FIG. 15 shows an example of microwave Fano-resonance spectroscopy based on the SRR structure.

DETAILED DESCRIPTION OF EMBODIMENTS OF THE INVENTION

The invention is a microwave-cavity method suitable for precise spectroscopic characterization of different types of lossy materials, including biological liquids. The method of the invention is based on the Fano-interference effect in a microwave structure with an embedded small ferrite-disk resonator.

According to the invention, a rectangular-waveguide microwave cavity with low-quality factor Q is used as a strongly damped oscillator, while a MDM ferrite disk (embedded into a microwave cavity) manifests itself as a weakly damped oscillator. Being a wave interference phenomenon, Fano resonance is highly sensitive to the scattering details of a system and can be used in the study of various transport properties. In the present invention, variation of the transport properties is due to different lossy samples loading the microwave cavity. Effective coupling between the two modes (strongly damped and weakly damped ones) results in a strong modulation of the cavity absorption spectrum. The lineshape of the peaks is highly dependent on the frequency of the MDM oscillation. When the frequency of the magnetic-dipolar-mode (MDM) resonance is not equal to the cavity resonance frequency, the asymmetric Fano-like lineshape of the peaks is obtained. Using a bias magnetic field to tune the MDM resonance frequency to the cavity resonance frequency, allows the symmetric Lorentz-like lineshape of the peaks to be observed. Use of an extremely narrow Lorentzian peak allows exact probing of the resonant frequency of a cavity loaded by a high-lossy-material sample. The cavity resonant frequency is the frequency of minimum power absorption of the cavity. For different kinds of samples, different frequencies of Lorentzian peaks are obtained. This gives a picture for precise spectroscopic characterization of high absorption matter in microwaves.

Figure 1A:
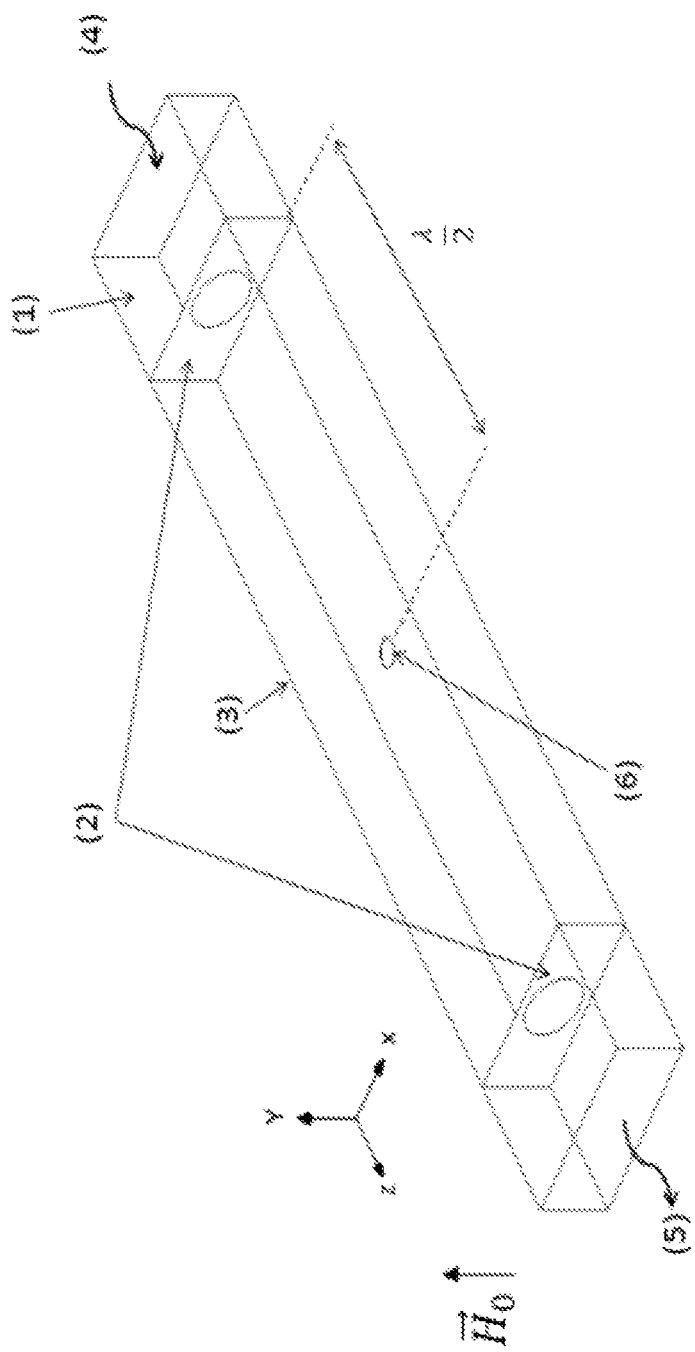
FIG. 1(a) shows a rectangular-waveguide microwave cavity with an enclosed yttrium-iron-garnet (YIG) disk.
Figure 1B:
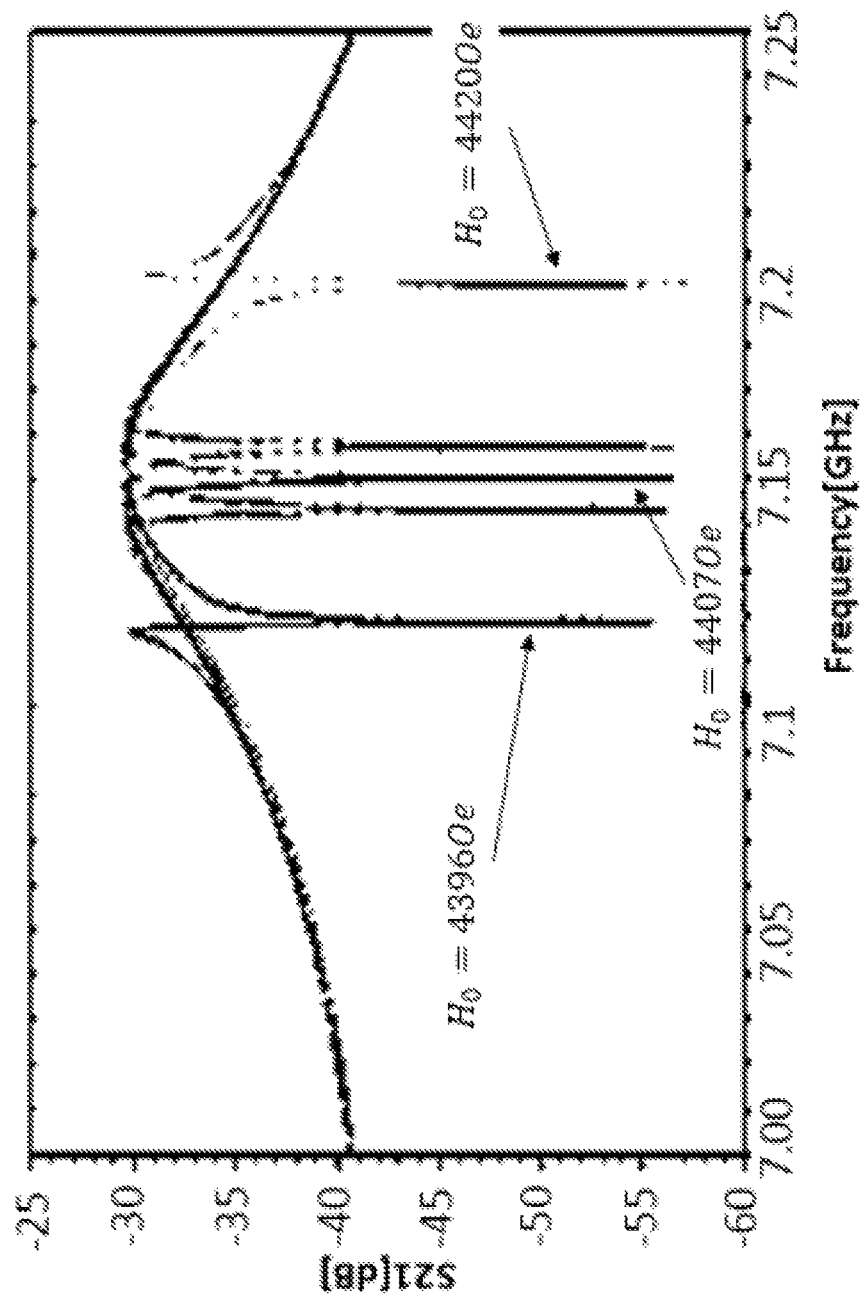
FIG. 1(b) shows the numerically obtained frequency characteristics of a transmission coefficient in the structure shown in FIG. 1(a)

FIG. 1a shows a rectangular waveguide 1 with two irises 2. A rectangular-waveguide cavity 3 with the $TE_{102}$ resonant mode is defined by the space between two irises 2. To excite the cavity, an input port 4 and an output port 5 are used. An yttrium-iron-garnet (YIG) disk 6 is embedded inside the rectangular waveguide cavity. The disk is biased by a normal dc magnetic field $\vec{H}_0$. The disk position is in a maximum of the RF magnetic field of the cavity. FIG. 1b shows the frequency characteristics of a transmission coefficient in the structure that is numerically obtained by use of a HFSS program. With tuning the MDM resonance frequency by a bias magnetic field strong transformation of line-shape of the peaks is observed. At frequencies of the MDM resonance not equal to the cavity resonance frequency, Fano-like transmission intensity is observed. When frequency of the MDM resonance is exactly equal to the cavity resonance frequency, a Lorentz-like line shape is observed.

From FIG. 1b it can be seen that coupling between a MDM resonance and electromagnetic (EM) cavity resonance results in appearance of destructive and constructive interferences. At the destructive interferences, the channels of EM waves propagating in a microwave cavity are effectively suppressed and a transmission coefficient in the structure is sharply reduced. There is a purely interference effect which is not related to the absorption by MDM oscillations. Since the uncoupled MDM resonance is extremely sharp, as compared to the EM-cavity-resonance width, the MDM damping can be set equal to zero. The observed quantum-like interference between the excitation pathways, that control the EM response, can be classified as electromagnetically induced non-transparency (in contrast to a well-known effect of electromagnetically induced transparency [33]). In the case of the constructive interferences, a level of a transmission coefficient in the structure is slightly increased.

Figure 2:
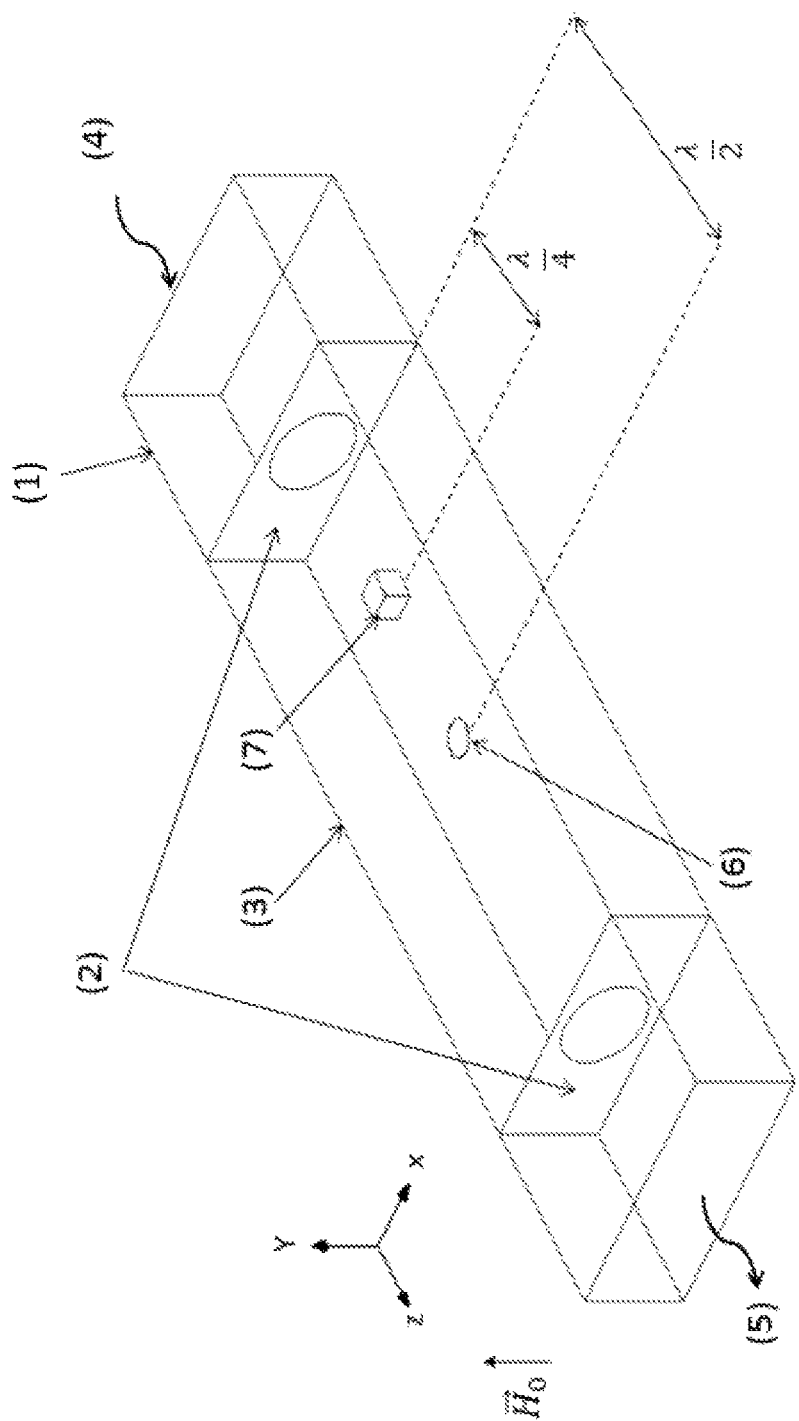
FIG. 2 schematically shows a setup that can be used to carry out the method of the invention.

FIG. 2 schematically shows a setup that was used to carry out experiments 1 to 5 described herein below that are presented to demonstrate the invention. The setup comprises a rectangular waveguide 1 with two irises 2. A rectangular-waveguide cavity 3 with the $TE_{102}$ resonant mode is defined by the space between two irises 2. To excite the cavity, an input port 4 and an output port 5 are used. An yttrium-iron-garnet (YIG) disk 6 is embedded inside the rectangular waveguide cavity. The ferrite disk has a diameter=3 mm. The YIG film thickness=49.6 μm. Saturation magnetization of a ferrite is $4\pi M_0=1880G$ and the linewidth is $\Delta H=0.8$ Oe. The disk is biased by a normal dc magnetic field $\vec{H}_0$. The disk axis is oriented along the waveguide E-field and the disk position is in a maximum of the RF magnetic field of the cavity. The cavity 3 is loaded by a dielectric sample 7 placed in a maximum of the RF electric field.

Experiment 1

The first experiment does not demonstrate the invention but is a demonstration of the above mentioned problems of the material characterization by using a standard perturbation technique. Without a bias magnetic field $\vec{H}_0$, a ferrite disk behaves as a small dielectric sample. Since a ferrite disk is placed in a maximum of the cavity RF magnetic field, its role (when $\vec{H}_0=0$) is negligibly small. FIG. 3a shows the frequency characteristics of a transmission coefficient when the cavity 3 is loaded with a small low-loss dielectric sample 7 ($S_{21}$ is a parameter of the scattering matrix). The samples measured were air ($\in_r=1$) and two ceramics disks having diameters of 3 mm and thickness of 2 m and dielectric constants $\in_r=30$ (K-30; TCI Cermics, Inc.) and $\in_r=50$ (K-30; TCI Cermics, Inc.). For such dielectric samples, the cavity is highly coherent and other "parasitic" scattering channels are less dominant, making the standard perturbation technique applicable. In this case, the cavity's quality factor is sufficiently large to detect the resonance shift and there is no need to use a ferrite disk for probing the exact resonance frequency. Furthermore, even if a bias magnetic field is not zero, the Fano-resonance effect does not occur in this case since the cavity cannot be considered to vary slowly at the vicinity of the MDM resonance band.

FIG. 3b shows the frequency characteristics of a transmission coefficient when the same dielectric samples (air; curve $\in_r=30$; $\in_r=50$) are wrapped by a high-absorption material 8—in this experiment polyurethane. In this case, a cavity quality factor is strongly reduced, the $TE_{102}$ mode becomes less dominant and resonance frequency shifts are not as clear as in the low loss scenario. Certainly, an exact characterization of the sample parameters by transformation of the spectral characteristics is impossible in this case.

FIG. 3c and FIG. 3d schematically show the experimental setup used to obtain FIG. 3a and FIG. 3b respectively. The sinusoidal curve 9 in FIG. 3c represents the electric field distribution in cavity 3.

Experiment 2

This experiment illustrates how the Fano-interference method of the invention can be used to detect the cavity resonance frequency when the cavity is loaded by a high-lossy material. FIG. 4b shows the experimental setup. In this case the sample is comprised of high-lossy wrapping material 8 shown symbolically surrounding air 10. A variable bias magnetic field, shown symbolically by the border 11 surrounding disk 6, is applied to the ferrite disk 6.

When a suitable bias magnetic field is switched on, the MDM spectral peaks of a ferrite disk are observed. FIG. 4a shows the positions of the main MDM peaks for different values of the bias magnetic field. It can be seen clearly that for magnetic field values $\vec{H}_0^{(1)}$ and $\vec{H}_0^{(2)}$ the same type of the peak line-shape that corresponds to the Fano asymmetry parameter q>0 is obtained.

While for a bias field $\vec{H}_0^{(4)}$ there is another type of the peak line-shape with the parameter q<0. A bias magnetic field $\vec{H}_0^{(3)}$ gives exactly a Lorentzian-like shape (q=0). The change of sign of the Fano asymmetry parameter is due to coupling between the narrow band resonator (the MDM ferrite disk 6) and a highly damped resonator (the $TE_{102}$-mode cavity 3 with a lossy-material sample 8). The ferrite disk 6 is not coupled with other scattering channels.

For $\vec{H}_0^{(3)} \equiv \vec{H}_0^{(Lorentz)}$ the resonance frequencies of the MDM disk and $TE_{102}$-mode cavity are equal. Therefore the value of the external parameter value $\vec{H}_0^{(3)} \equiv \vec{H}_0^{(Lorentz)}$ exactly equals the cavity resonance frequency. The meaning of this is that Fano-interference method of the invention can be used for precise spectroscopic characterization of high-lossy materials. The method does not give exact values of parameters $\in'$, $\in''$ and $\mu'$, $\mu''$. As discussed herein above, the physical meaning of these parameters is not clear for high-lossy material samples. Using the method of the invention it is possible to mark exactly the position of a very narrow Lorentz peak on the frequency axis corresponding to a certain type of a lossy material in the cavity. For different types of materials, one has different spectroscopic Lorentz-peak markers on the frequency axis.

Experiment 3

The purpose of this experiment is to show that by using the method of the invention different spectroscopic Lorentz-peak markers on the frequency axis are obtained for different materials. FIG. 5c schematically shows the experimental setup used for this experiment. It is essentially the same as FIG. 4b with the exception that the high loss wrapping material 9 (polyurethane) surrounds one of the two dielectric samples 8 ($\in_r=30$; $\in_r=50$) used in experiment 1 in addition to an air sample 10. The samples are placed in a maximum of the RF electric field of the cavity. For $\vec{H}_0=0$ the frequency characteristics of a transmission coefficient in the cavity are shown in FIG. 3b. When a bias magnetic field is switched on, these characteristics remains generally the same, but sharp MDM peaks additionally appear as can be seen in FIG. 5a. With variation of the bias field a Lorentz-peak bias field is obtained for every type of a high-lossy material sample. The frequency of each Lorentz-peak marks exactly the cavity resonance frequency for the specific material loading the cavity (curve a—air; curve b—$\in_r=30$; curve c—$\in_r=50a$).

FIG. 5a shows spectroscopic curves for three different high-lossy material samples. The spectra are obtained for the main MDM of a ferrite disk. To increase sensitivity of the spectroscopic analysis, the frequency characteristics are normalized to the background (when $\vec{H}_0=0$) transmission characteristics. FIG. 5b shows the normalized spectroscopic curves. The frequencies shown in FIG. 5a and FIG. 5b are: $f_1=6.811$ GHz, $f_2=6.762$ GHz, $f_3=6.737$ GHz.

Experiment 4

The possibility of using the Fano-interference method of the invention for spectroscopic signature of biological liquids is well illustrated by experiments carried out with salt and glucose solutions. FIG. 6d shows the experimental setup, which is identical to that of FIG. 5c with the exception of the type of sample used.

Figure 6A:
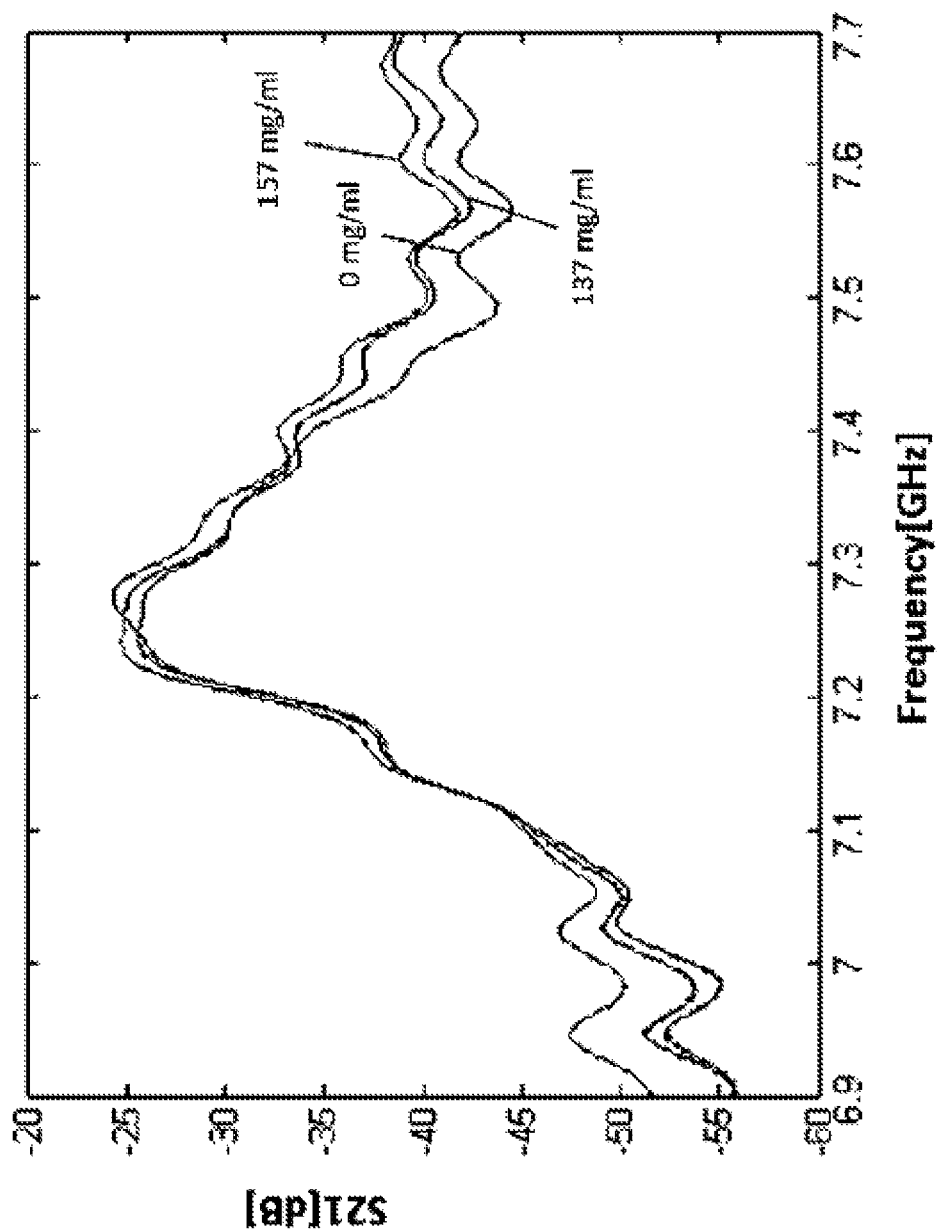
FIG. 6a shows the frequency characteristics of a transmission coefficient of a cavity loaded by a small capsule containing solutions of different concentrations of salt in distilled water with the bias magnetic field on the ferrite disk $\vec{H}_0=0$.
Figure 6B:
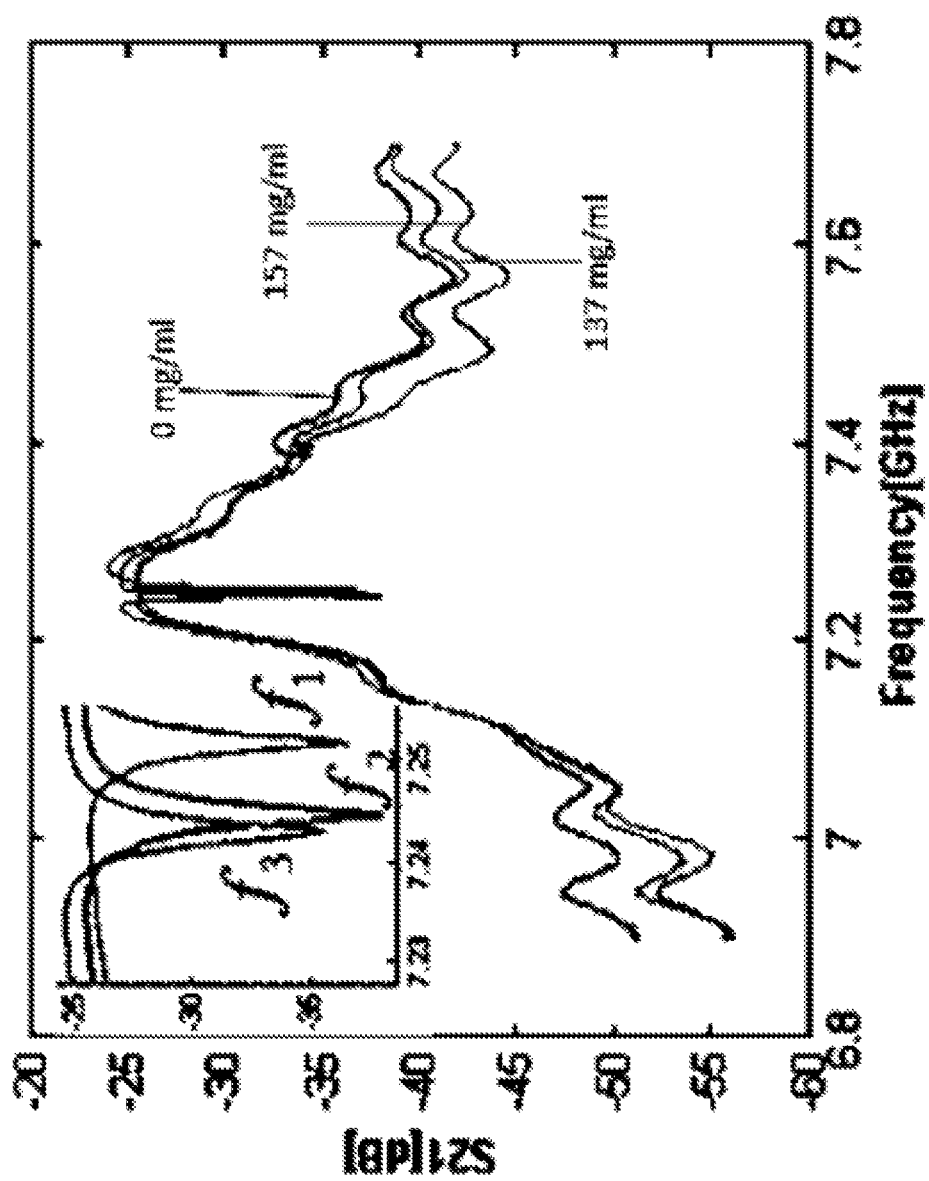
FIG. 6b shows the Lorentz peaks obtained for the same samples as in FIG. 6a when specific values of the bias magnetic field are applied to the ferrite disk.
Figure 6C:
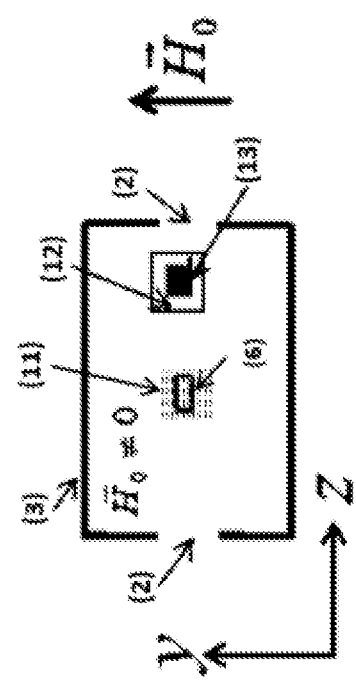
FIG. 6c shows the normalized spectroscopic curves shown in FIG. 6b.
Figure 6D:
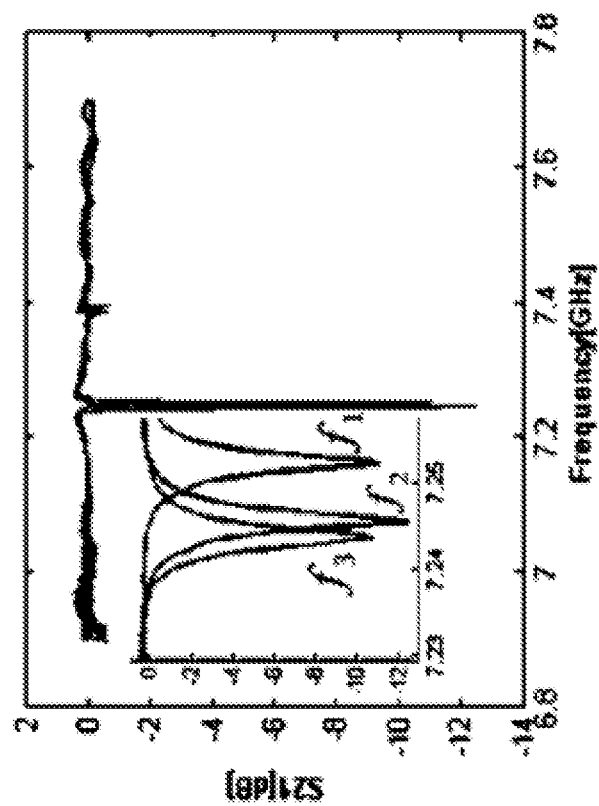
FIG. 6d schematically shows the experimental setup used to obtain the results shown in FIG. 6a, FIG. 6b, and FIG. 6c.

FIG. 6a shows the frequency characteristics of a transmission coefficient of a cavity loaded by a small capsule 12 containing solutions of different concentrations of salt in distilled water. The capsule is a small cylinder (length 3 mm, internal diameter 1.5 mm, and wall thickness 0.2 mm) made of polyethylene. The capsule 12 is filled with distilled water (salt concentration=0) and salt solutions (concentrations: 137 mg/ml and 157 mg/ml). The capsule is placed in a maximum of the RF electric field of the cavity and the bias magnetic field is $\vec{H}_0=0$. From FIG. 6a it can be seen that precise spectroscopic characterization of these solutions is not possible. The Lorentz peaks in FIG. 6b and the normalized spectroscopic curves shown in FIG. 6c allow exact characterization of the salt concentration. These peaks are the cavity resonance frequencies obtained for specific values of the bias magnetic field applied to the ferrite disk. The frequencies shown in FIG. 6b and FIG. 6c are: $f_1=7.252$ GHz, $f_2=7.245$ GHz, $f_3=7.244$ GHz.

Experiment 5

Figure 7D:
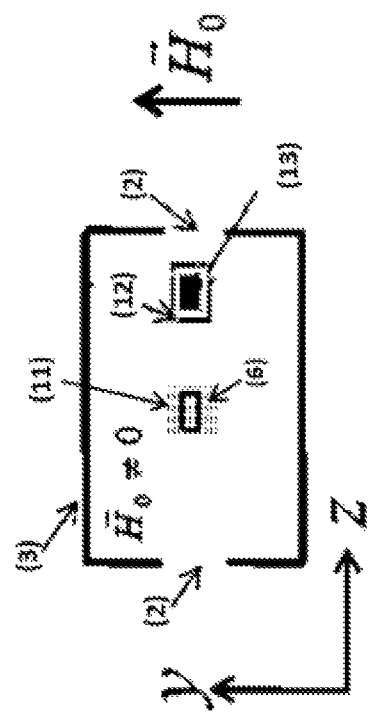
Figure 7C:
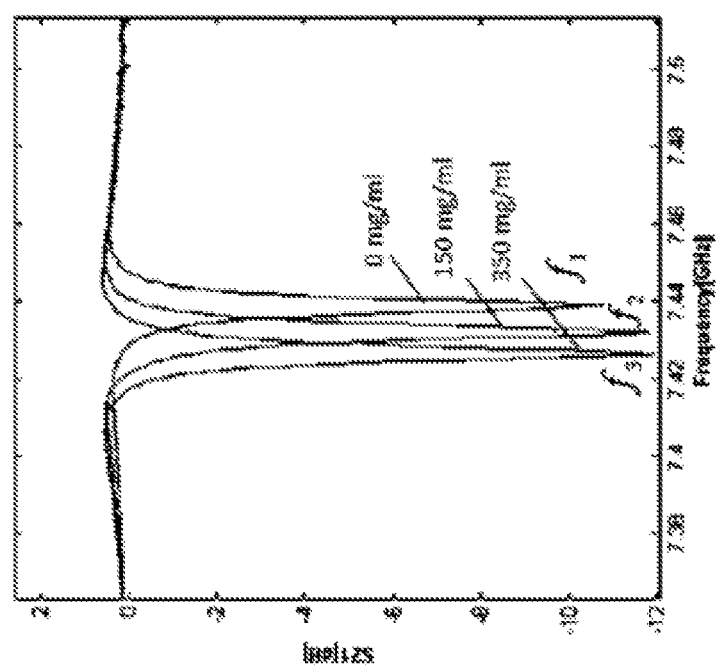

This experiment is identical to experiment 4 with the exception that in this case the sample is a small capsule filled with distilled water (concentration=0) and glucose solutions (concentrations: 150 mg/ml and 350 mg/ml). FIG. 7a to FIG. 7d correspond to FIG. 6a to FIG. 6d The frequencies shown in FIG. 7b and FIG. 7c are: $f_1=7.439$ GHz, $f_2=7.432$ GHz, $f_3=7.426$ GHz.

Figure 8:
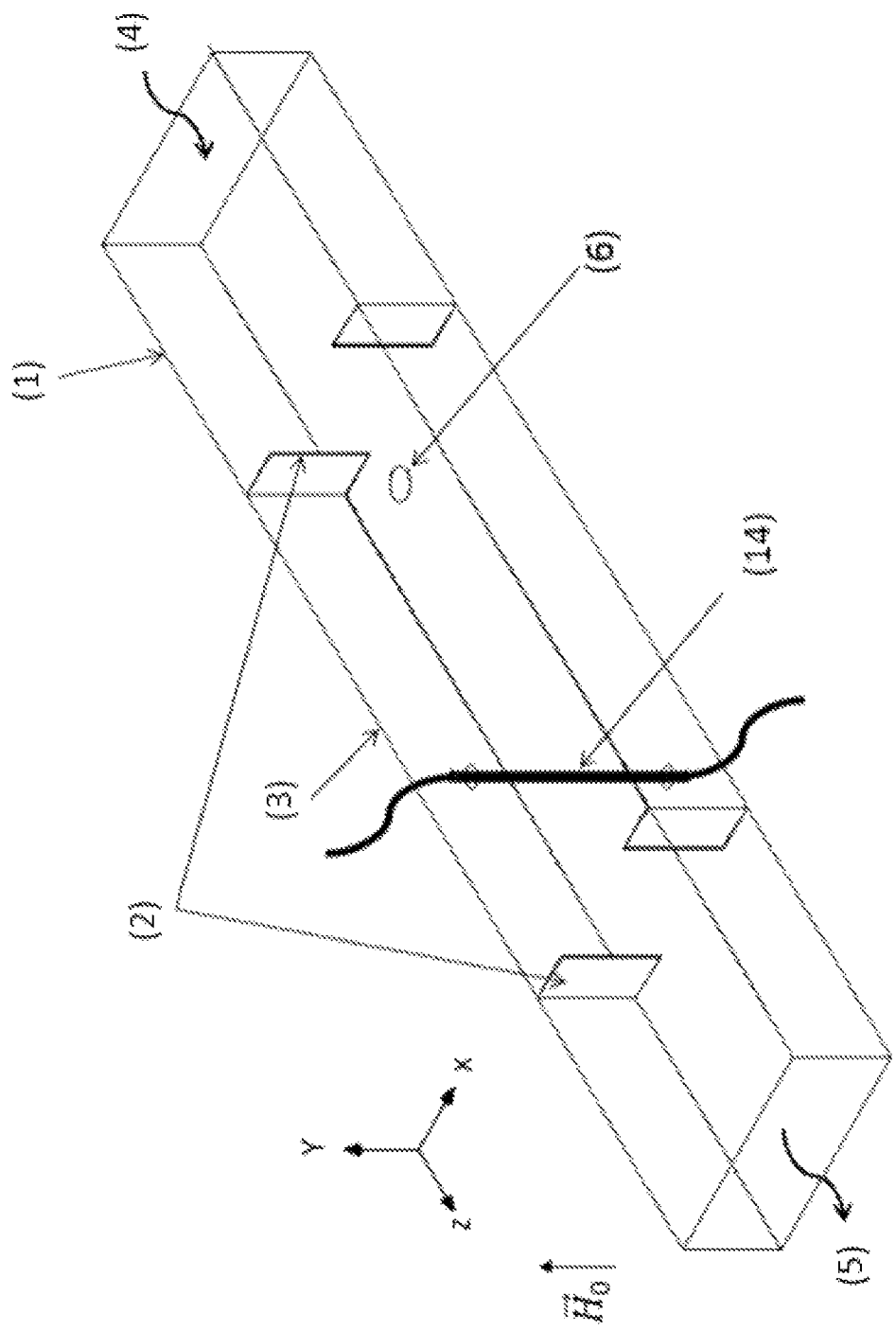
FIG. 8 schematically shows a waveguide that can be used for microwave sensing of continuous fluidic flows according to an embodiment of the invention.

FIG. 8 schematically shows a waveguide that can be used to carry out experiments 6 to 8 described herein below for microwave sensing of continuous fluidic flows. The setup comprises a rectangular waveguide 1 with two irises 2. A rectangular-waveguide cavity 3 with the $TE_{102}$ resonant mode is defined by the space between two irises 2. To excite the cavity, an input port 4 and an output port 5 are used. An yttrium-iron-garnet (YIG) disk 6 is embedded inside the rectangular waveguide cavity. The ferrite disk has a diameter=3 mm. The YIG film thickness=49.6 μm. Saturation magnetization of a ferrite is $4\pi M_0=1880$ G and the line width is $\Delta H=0.8$ Oe. The disk is biased by a normal dc magnetic field $\vec{H}_0$. The disk axis is oriented along the waveguide E-field and the disk position is in a maximum of the RF magnetic field of the cavity. The cavity 3 is loaded by a silicon tube 14 through which liquid flows placed in a maximum of the RF electric field of the cavity. The tube has a diameter of 2 mm. The flowing liquid interacts with the cavity in a region of about 5 mm.

Figure 9:
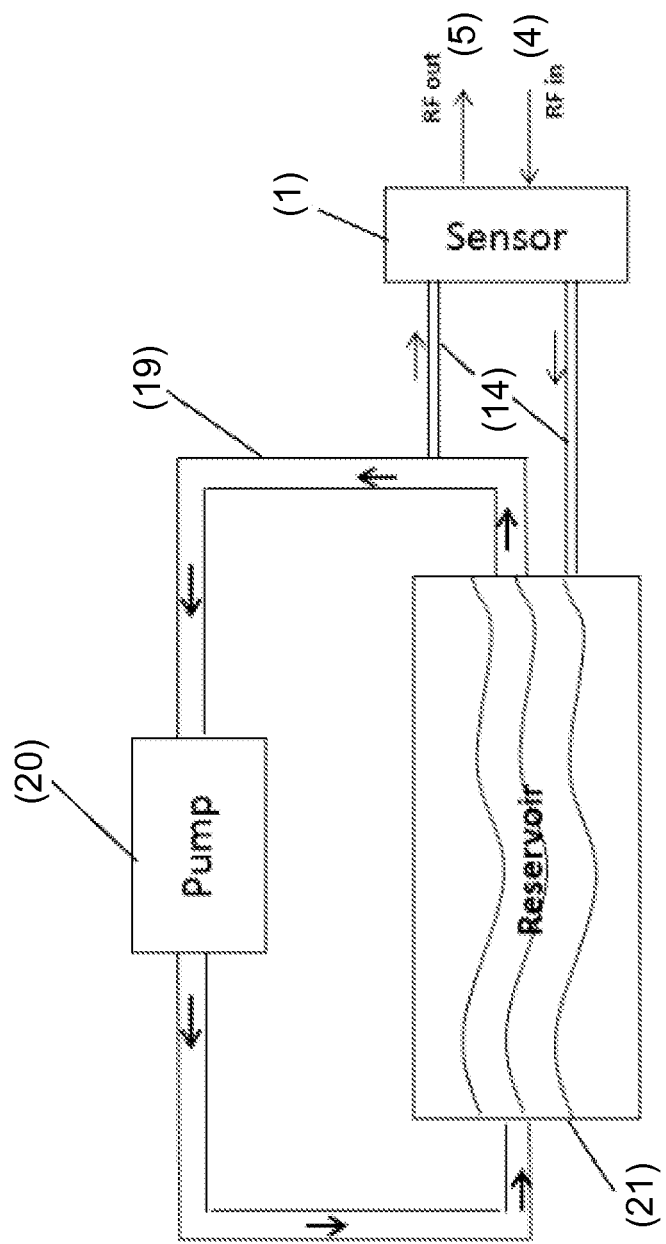
FIG. 9 schematically shows an experimental setup for characterization of high-loss liquid parameters for liquid continuously flowing through the rectangular waveguide of FIG. 8.

FIG. 9 schematically shows an experimental setup for characterization of high-loss liquid parameters for liquid continuously flowing through the rectangular waveguide of FIG. 8. Seen in the figure are waveguide 1, main line 19, pump 20, and reservoir 21 that are connected together to continuously circulate the liquid to be analyzed through silicon tube 14. Not shown are the power supplies and control circuitry that supplies RF input 4 to waveguide 1 or the circuitry, processor, software, and display means that are adapted to receive the RF output 5 from waveguide 1 and process the output to produce a Fano-resonance spectrum of the liquid.

The measurement of liquid parameters is done by variation of the external DC magnetic field. The relevant magnetic field intensity values are defined by scanning elements of the vector $[H_0]$ $$[H_0]=[H_0^1,H_0^2,\ldots H_0^M], \quad (4)$$

where M is the number of values of the external DC magnetics fields in the scan. For each $H_0^i$ we have the output scattering-matrix variable $S_{21}$ as a vector of normalized spectrum amplitudes [S]:

$$[S]=[S^1 S^2 \ldots S^M] \quad (5)$$

and a vector of frequencies [f]:

$$[f]=[f^1 f^2 \ldots f^N], \quad (6)$$

where N is a total number of the frequency samples in the Fano-resonance characteristic. Since at the Lorentz resonance the normalized spectrum should be symmetrical, we divide the vector [S] around the minimum point as follows:

$$[S]=[S^1 S^2 \ldots S^{P-1} S^P S^{P+1} \ldots S^N], \quad (7)$$

where P is the index of the minimum component of the vector [S].

There are several ways to approximate the symmetry of the spectrum. As an example around the minimum point the MSE algorithm can be used, as follows:

$$\text{Error} = \sum_{q=1}^{P} |S^{P-q} - S^{P+q}|. \quad (8)$$

The Error is a measure of asymmetry; therefore, the lower the Error the greater the symmetry. It is assumed that Lorentz-resonance response occurs at the minimum of Error.

Figure 10B:
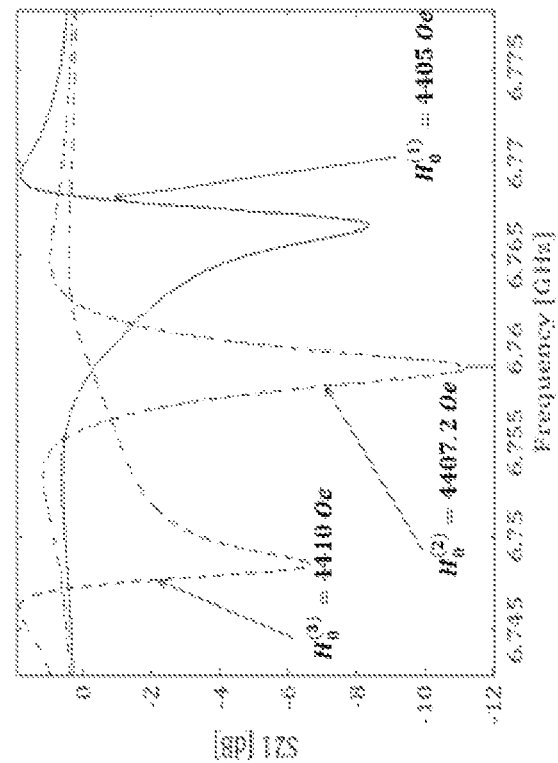
FIG. 10a and FIG. 10b illustrate the measurement algorithm for obtaining the cavity resonance frequency.
Figure 10A:
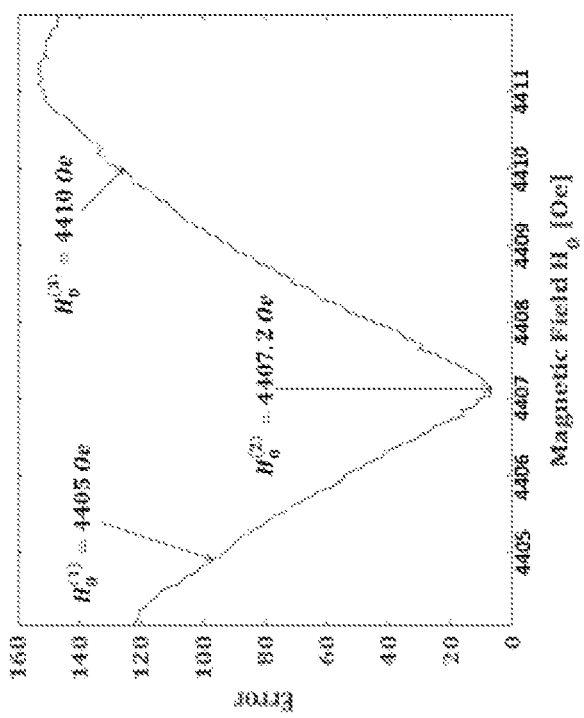

FIG. 10a and FIG. 10b illustrate the measurement algorithm for obtaining the cavity resonance frequency.

FIG. 10a shows the error for each scan, where the error represents the unsymmetrical shape of the resonance. The different values for the error at each scan are caused by the different DC magnetic fields applied to the ferrite disk. The goal of the measurements is to locate the scan number in which Lorentz resonance takes place. At Lorenz resonance we have a symmetrical shape, therefore scan in which the Lorentz shape occurs is the one that has the minimum of asymmetry i.e. the minimum error. From Figure (a) it can be seen that Error(1) is approximately 95, Error(3) is 125 and Error(2) is the minimum error.

FIG. 10b shows an example of three different scans It is easy to see from FIG. 10b the asymmetry of the shapes corresponding to $H_0^1$ and $H_0^3$ the symmetrical, i.e. Lorentz shape corresponding to $H_0^2$. As shown in the results of the experiments described herein, once the frequency of the Lorentz resonance is known from FIG. 10b, the concentration of components of the solution can be determined precisely.

Experiment 6

Figures 11A, 11B:
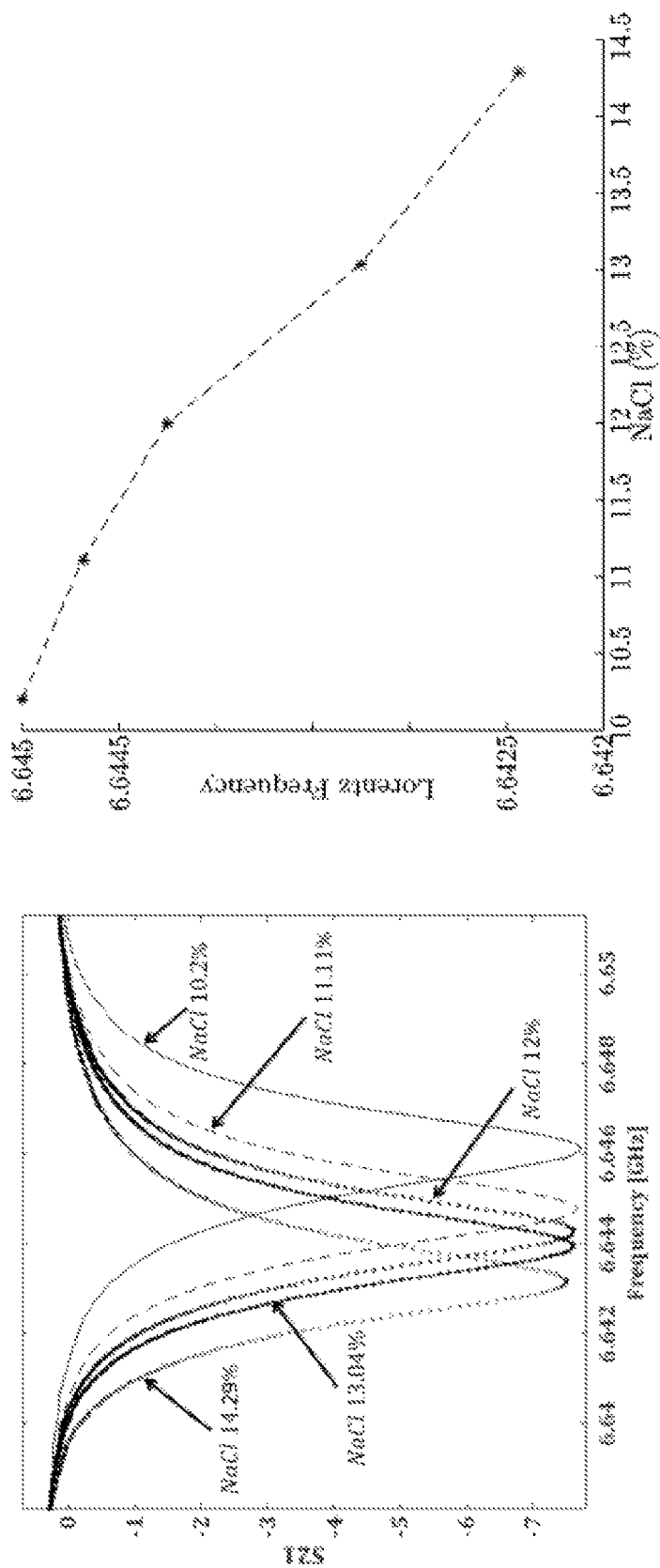

FIG. 11a shows the Lorentz frequencies for different concentrations of NaCl in water. FIG. 11b is a graph of Lorentz frequencies vs. concentration derived from the results shown in FIG. 11a.

Experiment 7

Figure 12B:
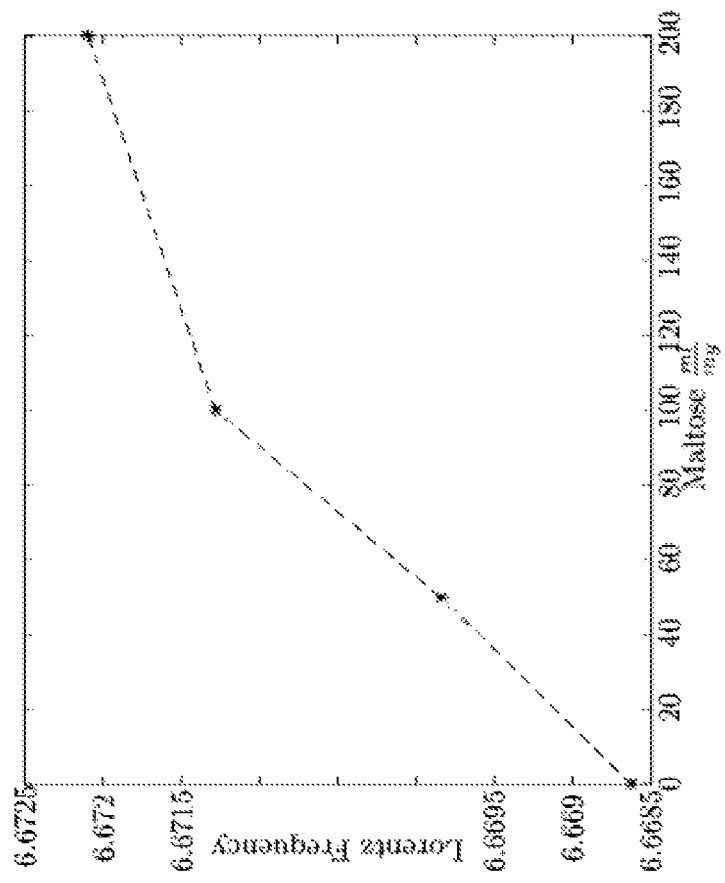
Figure 12A:
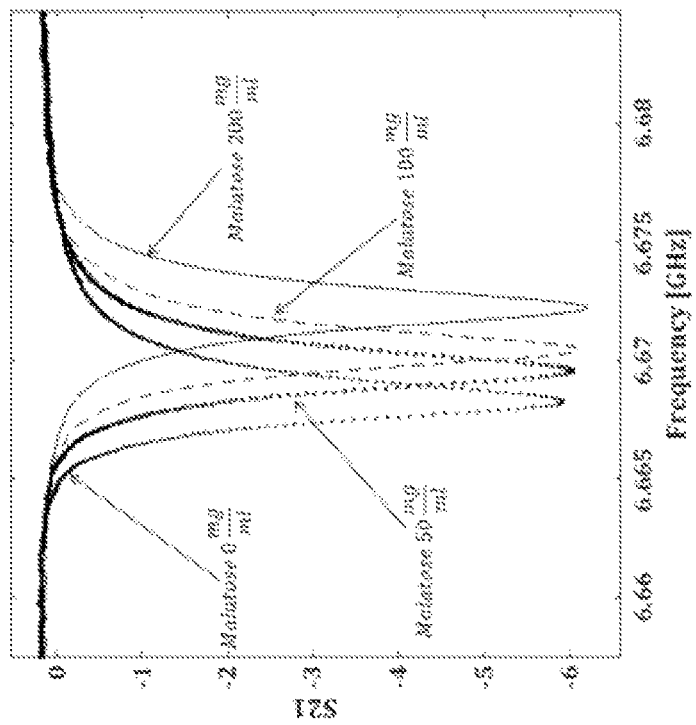
FIG. 12a shows the Lorentz frequencies for different concentrations of Malatose in water.

FIG. 12a shows the Lorentz frequencies for different concentrations of Malatose in water. FIG. 12b is a graph of Lorentz frequencies vs. concentration derived from the results shown in FIG. 12a.

Experiment 8

FIG. 13a shows the Lorentz frequencies for different concentrations of Diesel fuel concentration in solution with oil in water. FIG. 13b is a graph of Lorentz frequencies vs. concentration derived from the results shown in FIG. 13a.

Nowadays, microwave biosensing is mainly represented by the microwave-resonator technique and the transmission/reflection technique [9-11, 35]. The split ring resonator (SRR) is considered to be one of the fundamental building blocks of engineered electromagnetic meta-materials. It usually constitutes a metallic open loop with a gap. At resonance, the SRR possesses an intense electric field component at the gap region, making the resonance frequency and bandwidth of the SRR sensitive to different dielectric samples placed at the vicinity of the gap [11, 35]. This feature, along with its subwavelength dimensions makes the SRR a promising planar sensor to be implemented in applications such as dielectric sensing and lab-on-a-chip devices. A major fault with using the SRR as a planar sensor is its low quality factor (due to the microstrip open structure characteristic), which is of the order of 100. When measuring biological samples, which typically possess high concentration of water and hence high losses, the SRR's quality factor further degrades, making it unsuitable for such measurements. The method of Fano-resonance spectroscopy of the invention can be successfully used for the measurement of absorptive samples implanted upon a planar SRR sensor.

Figure 14:
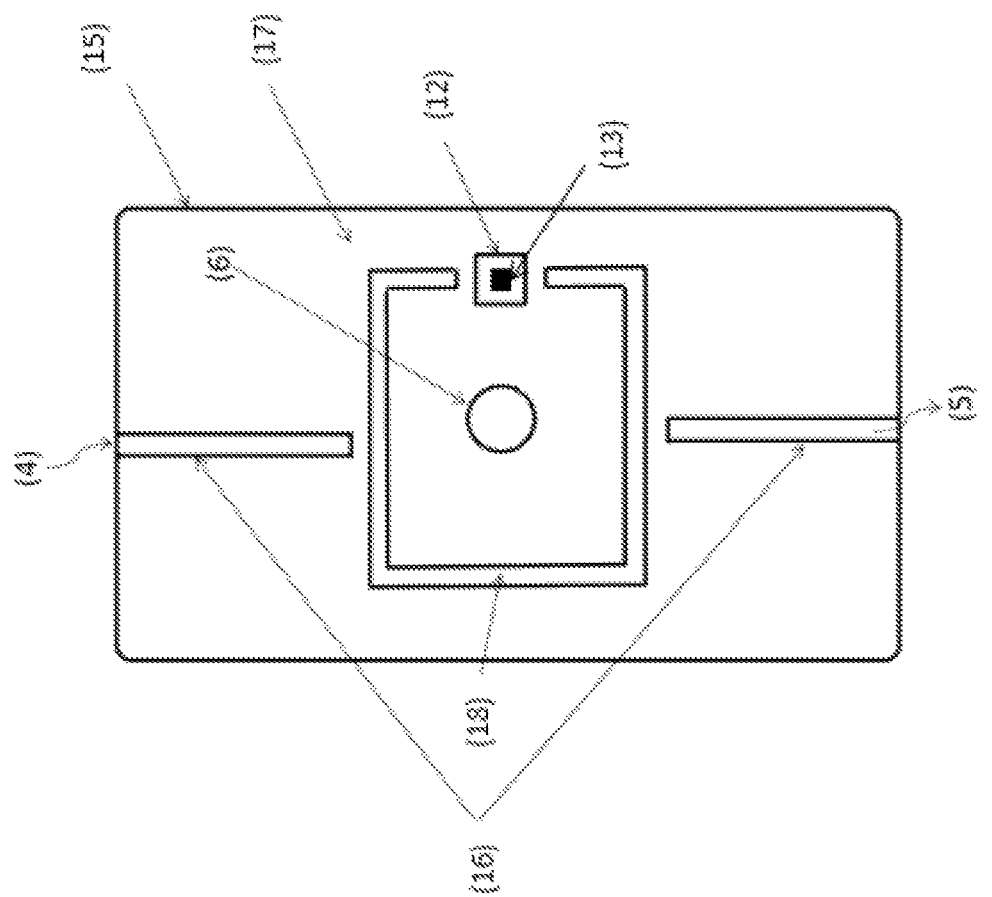
FIG. 14 schematically shows a microstrip structure for carrying out Fano-resonance for the measurement of absorptive samples implanted upon a planar SRR sensor.

FIG. 14 shows a microstrip structure 15 with conducting strips 16 on a dielectric substrate 17. Conducting strips 16 are coupled with the split ring resonator (SRR) 18. To excite a SRR, an input port 4 and an output port 5 are used. An yttrium-iron-garnet (YIG) disk 6 is embedded inside the SRR. The SRR 18 is loaded by a small capsule 12. The capsule 12 is filled with liquid 13.

Experiment 9

FIG. 15 shows an example of microwave Fano-resonance spectroscopy based on the SRR structure. The figure shows experimental measurement of the transmission characteristic of different concentrations of glucose in water. A Lorentzian line shape for each glucose sample is established as the magnetic bias field is swept, where $H_0^{(1)} < H_0^{(2)} < H_0^{(3)}$.

Although embodiments of the invention have been described by way of illustration, it will be understood that the invention may be carried out with many variations, modifications, and adaptations, without exceeding the scope of the claims.

BIBLIOGRAPHY

[1] U. Fano, Phys. Rev. 124, 1866 (1961).
[2] C. Wu, A. B. Khanikaev, R. Adato, N. Arju, A. A. Yanik, H. Altug, and G. Shvets, Nature Mater. 11, 69 (2012).
[3] A. E. Cetin and H. Altug, ASC Nano 6, 9989 (2012).
[4] S. Ray and J. Behari, Phys. Med. Biol. 31, 1031 (1986).
[5] L. L. van Zandt, Phys. Rev. Lett. 57, 2085 (1986).
[6] C.-T. Zhang, Phys. Rev. A 40, 2148 (1989).
[7] C. Gabriel, E. H. Grant, R. Tata, P. R. Brown, B. Gestblom, and E. Noreland, Biophys. J. 55, 29 (1989).
[8] R. K. Adair, Biophys. J. 82, 1147 (2002).
[9] J. Kim, A. Babajanyan, A. Hovsepyan, K. Lee, and B. Friedman. Rev. Sci. Instr. 79, 086107 (2008).
[10] C. Dalmav, M. Cherav, A. Pothier, F. Lalloué, M. O. Jauberteau, P. Blondy, Sens. Actuat. A: Phys. 162, 189 (2010).
[11] H.-J. Lee, H.-S. Lee, K.-H. Yoo, and J.-G. Yook, J. Appl. Phys. 108, 014908 (2010).
[12] H.-J. Lee, J.-H. Lee, and H.-I. Jung, Appl. Phys. Lett. 99, 163703 (2011).
[13] S. Kim, J. Kim, K. Kim, J.-H. Lee, A. Babajanyan, B. Friedman, K. Lee, Curr. Appl. Phys. 14, 563 (2014).
[14] B. Yu. Kapilevich, S. G. Ogourtsov, V. G. Belenky, A. B. Maslenikov, and A. S. Omar, IEEE Trans. Microw. Theor. Techn. 48, 2159 (2000).

[15] E. Ermilova, F. F. Bier and R. Hölzel, Phys. Chem. Chem. Phys. 16, 11256 (2014).
[16] L. D. Landau and E. M. Lifshitz, *Electrodynamics of Continuous Media*, 2nd ed. (Pergamon Press, Oxford, 1984).
[17] E. O. Kamenetskii, Phys. Rev. E 63, 066612 (2001).
[18] E. O. Kamenetskii, M. Sigalov, and R. Shavit, J. Phys.: Condens. Matter 17, 2211 (2005).
[19] E. O. Kamenetskii, J. Phys. A: Math. Theor. 40, 6539, (2007).
[20] E. O. Kamenetskii, M. Sigalov, and R. Shavit, Phys. Rev. A 81, 053823 (2010).
[21] E. O. Kamenetskii, J. Phys.: Condens. Matter 22, 486005 (2010).
[22] E. O. Kamenetskii, R. Joffe, and R. Shavit, Phys. Rev. A 84, 023836 (2011).
[23] E. O. Kamenetskii, E. O., R. Joffe, and R. Shavit, Phys. Rev. E 87, 023201, (2013).
[24] E. O. Kamenetskii, A. K. Saha, and I. Awai, Phys. Lett. A 332, 303 (2004).
[25] M. Sigalov, E. O. Kamenetskii, and R. Shavit, Appl. Phys. B 93, 339 (2008).
[26] M. Berezin, E. O. Kamenetskii, and R. Shavit, Phys. Rev. E 89, 023207 (2014).
[27] E. O. Kamenetskii, G. Vaisman, and R. Shavit, J. Appl. Phys. 114, 173902 (2013).
[28] M. Sigalov, E. O. Kamenetskii, and R. Shavit, J. Phys.: Condens. Matter 21, 016003 (2009).
[29] E. O. Kamenetskii, M. Sigalov, and R. Shavit, J. Appl. Phys. 105, 013537 (2009).
[30] J. F. Dillon, J. Appl. Phys. 31, 1605 (1960).
[31] T. Yukawa and K. Abe, J. Appl. Phys. 45, 3146 (1974).
[32] S. E. Harris, Phys. Today 50, 36 (1997).
[33] R. Hutcheon, M. de Jong, and F. Adams, J. Microw. Power Electromagn. Energy 27, 87 (1992).
[34] G. Vaisman, E. O. Kamenetskii, and R. Shavit, "Magnetic-dipolar-mode Fano resonances for microwave spectroscopy of high absorption matter", J. Phys. D: Appl. Phys. 48, 115003 (2015).
[35] H. Torun, F. C. Top, G. Dundar, and A. D. Yalcinkaya, J. Appl. Phys. 116, 124701 (2014).

The invention claimed is:

1. A method of Fano resonance microwave spectroscopy of high absorption matter comprising:
   a) providing a waveguide microwave cavity with low-quality factor used as a strongly damped oscillator;
   b) embedding a magnetic-dipolar-mode (MDM) ferrite disk used as a weakly damped oscillator in the microwave cavity;
   c) loading the microwave cavity with a sample of high absorption matter, wherein there is no mechanical contact between the MDM disk and the sample;
   d) exciting the waveguide microwave cavity with microwave energy that creates a radio frequency (RF) electromagnetic (EM) field having a resonance frequency in the waveguide microwave cavity;
   e) providing a variable bias magnetic field to tune the MDM resonance frequency of the ferrite disk to the resonance frequency of the cavity; and
   f) observing symmetric Lorentzian lineshapes of resonance absorption peaks of the high absorption matter that are obtained by coupling of strongly damped oscillator modes of the waveguide microwave cavity and weakly damped oscillator modes of the MDM ferrite disk.

2. The method of claim 1, wherein the waveguide microwave cavity is a rectangular waveguide microwave cavity operated in a $TE_{102}$ resonant mode.

3. The method of claim 1, wherein the magnetic-dipolar-mode (MDM) ferrite disk is comprised of yttrium-iron-garnet (YIG).

4. The method of claim 1, wherein the bias magnetic field is a dc magnetic field applied at right angles to the flat surface of the magnetic-dipolar-mode (MDM) ferrite disk.

5. The method of claim 1, wherein the magnetic-dipolar-mode (MDM) ferrite disk is located at a maximum of a RF magnetic field of the EM field of the rectangular waveguide microwave cavity.

6. The method of claim 1, wherein the sample of the high absorption matter is located at a maximum of a RF electric field of the EM field of the rectangular waveguide microwave cavity.

7. The method of claim 1, wherein the sample of the high absorption matter is a liquid.

8. The method of claim 7, wherein the liquid is enclosed in a small capsule.

9. The method of claim 8, wherein the liquid continuously flows through the rectangular waveguide microwave cavity via a small diameter tube.

10. An apparatus for carrying out the method of claim 1, the apparatus comprising:
    a) a rectangular waveguide;
    b) two irises spaced apart in the waveguide;
    c) a rectangular waveguide microwave cavity defined by the space between the two irises;
    d) a RF input port at a first end of the waveguide configured to allow microwave energy that creates a radio frequency (RF) electromagnetic (EM) field having a resonance frequency to enter the waveguide microwave cavity;
    e) a RF output port at a second end of the waveguide configured to allow microwave energy to exit the waveguide microwave cavity;
    f) a yttrium-iron-garnet (YIG) disk locate at a maximum of the RF magnetic field of the rectangular waveguide cavity;
    g) a variable bias magnetic field to tune a MDM resonance of the YIG disk; and
    h) a dielectric sample located at a maximum of the RF electric field of the rectangular waveguide cavity.

11. The apparatus of claim 10 wherein the dielectric sample is a liquid enclosed in a small capsule.

12. The apparatus of claim 11 wherein the dielectric sample is a liquid that continuously flows through the rectangular waveguide microwave cavity via a small diameter tube.

13. The apparatus of claim 12 additionally comprising a pump, a reservoir and a main line that are connected together to continuously circulate the liquid through the small diameter tube.

14. A microstrip structure for carrying out the method of claim 1, the microstrip structure comprising:
    a) a dielectric substrate;
    b) a split ring resonator (SRR) comprised of a metallic open loop with a gap created on the substrate;
    c) a first conducting strip created on the substrate, the first conducting strip connected to a first side of the SSR adjacent to the side of the SSR comprising the gap;
    d) a second conducting strip created on the substrate, the second conducting strip connected to a second side of the SSR opposite to the side of the SSR to which the first conducting strip is connected;

e) a RF input port connected to the first conducting strip, the RF input port configured to allow microwave energy that creates a radio frequency (RF) electromagnetic (EM) field having a resonance frequency to enter the SRR via the first conducting strip;
f) a RF output port connected to the second conducting strip, the RF output port configured to allow microwave energy to exit the SRR via the second conducting strip;
g) an yttrium-iron-garnet (YIG) disk embedded inside the SRR; and
h) a small capsule filled with liquid loaded into the gap of the SRR.

\* \* \* \* \*